United States Patent
Eriksson et al.

(10) Patent No.: US 7,132,434 B2
(45) Date of Patent: Nov. 7, 2006

(54) METALLOPROTEINASE INHIBITORS

(75) Inventors: Anders Eriksson, Lund (SE); Matti Lepistö, Lund (SE); Michael Lundkvist, Lund (SE); Magnus Munck Af Rosenschöld, Lund (SE); Kristina Stenvall, Lund (SE); Pavol Zlatoidsky, Lund (SE)

(73) Assignee: AstraZeneca AB (SE)

( * ) Notice: Subject to any disclaimer, the term of this patent is extended or adjusted under 35 U.S.C. 154(b) by 58 days.

(21) Appl. No.: 10/494,645

(22) PCT Filed: Nov. 6, 2002

(86) PCT No.: PCT/SE02/02023

§ 371 (c)(1),
(2), (4) Date: May 5, 2004

(87) PCT Pub. No.: WO03/040098

PCT Pub. Date: May 15, 2003

(65) Prior Publication Data

US 2005/0026990 A1  Feb. 3, 2005

(30) Foreign Application Priority Data

Nov. 7, 2001 (SE) .................................. 0103710

(51) Int. Cl.
- A61K 31/454 (2006.01)
- A61K 31/4025 (2006.01)
- C07D 207/46 (2006.01)
- C07D 403/12 (2006.01)
- C07D 403/13 (2006.01)
- C07D 405/02 (2006.01)
- C07D 405/14 (2006.01)
- C07D 401/02 (2006.01)
- C07D 401/14 (2006.01)

(52) U.S. Cl. .............. 514/326; 514/422; 514/423; 548/423; 548/530; 546/208; 546/278.4; 544/360; 544/372

(58) Field of Classification Search ............ 514/326, 514/423, 422; 544/360, 372; 546/208, 278; 548/423, 530
See application file for complete search history.

(56) References Cited

U.S. PATENT DOCUMENTS

| | | | |
|---|---|---|---|
| 2,745,875 A | 5/1956 | Ehrhart et al. | |
| 3,452,040 A | 6/1969 | Langis | |
| 3,529,019 A | 9/1970 | Suh et al. | |
| 3,849,574 A | 11/1974 | Suh et al. | |
| 4,241,073 A | 12/1980 | Jamieson et al. | |
| 4,315,031 A | 2/1982 | Vincent et al. | |
| 5,068,187 A | 11/1991 | Takeichi et al. | |
| 5,246,943 A | 9/1993 | Blankley et al. | |
| 5,308,853 A | 5/1994 | Hodges et al. | |
| 5,521,187 A | 5/1996 | Freyne et al. | |
| 5,804,593 A | 9/1998 | Warpehoski et al. | |
| 5,917,790 A | 6/1999 | Ohta et al. | |
| 5,955,435 A | 9/1999 | Baxter et al. | |
| 6,046,214 A | 4/2000 | Kristiansen et al. | |
| 6,048,841 A | 4/2000 | Baxter et al. | |
| 6,114,361 A | 9/2000 | Robinson et al. | |
| 6,159,995 A | 12/2000 | Thorwart et al. | |
| 6,166,041 A | 12/2000 | Cavalla et al. | |
| 6,218,418 B1 | 4/2001 | Pevarello et al. | |
| 6,268,379 B1 | 7/2001 | Xue et al. | |
| 6,277,987 B1 | 8/2001 | Kukkola et al. | |
| 6,329,418 B1 | 12/2001 | Cheng et al. | |
| 6,339,101 B1 | 1/2002 | Ross et al. | |
| 6,340,691 B1 | 1/2002 | Levin et al. | |
| 6,429,213 B1 | 8/2002 | Xue et al. | |
| 6,890,915 B1 | 5/2005 | Sheppeck et al. | |
| 6,906,053 B1 | 6/2005 | Sheppeck et al. | |
| 2002/0006920 A1 | 1/2002 | Robinson et al. | |
| 2002/0028835 A1 | 3/2002 | Hu et al. | |
| 2002/0065219 A1 | 5/2002 | Naidu et al. | |
| 2002/0091107 A1 | 7/2002 | Madar et al. | |
| 2003/0130273 A1 | 7/2003 | Sheppeck et al. | |
| 2004/0106659 A1 | 6/2004 | Af Rosenschold | |
| 2004/0110809 A1 | 6/2004 | Lepisto et al. | |
| 2004/0116486 A1 | 6/2004 | Lepisto et al. | |
| 2004/0127528 A1 | 7/2004 | Eriksson et al. | |
| 2004/0138276 A1 | 7/2004 | Eriksson et al. | |
| 2004/0147573 A1 | 7/2004 | Eriksson et al. | |
| 2004/0152697 A1* | 8/2004 | Chan et al. ............. 514/227.8 | |

(Continued)

FOREIGN PATENT DOCUMENTS

EP  212617  8/1986

(Continued)

OTHER PUBLICATIONS

Aimoto, et al. "Synthesis of Carriers of Differing Strokes Radius with Activated Acyl Groups for Use as Reagents in Labeling Membrane Proteins," Journal of Biological Chemistry, vol. 256(10), pp. 5134-5143, 1981.*

(Continued)

*Primary Examiner*—Kamal A. Saeed
*Assistant Examiner*—Nyeemah Grazier
(74) *Attorney, Agent, or Firm*—Fish & Richardson P.C.

(57) ABSTRACT

Compounds of the formula (I), useful as metal-loproteinase inhibitors, especially as inhibitors of MMP12

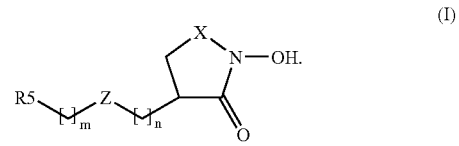

21 Claims, No Drawings

U.S. PATENT DOCUMENTS

| | | |
|---|---|---|
| 2004/0209874 A1 | 10/2004 | Sheppeck et al. |
| 2005/0019994 A1 | 1/2005 | Chang |
| 2005/0171096 A1 | 8/2005 | Sheppeck et al. |
| 2005/0245586 A1 | 11/2005 | Henriksson et al. |
| 2005/0256176 A1 | 11/2005 | Burrows et al. |
| 2006/0063818 A1 | 3/2006 | Burrows et al. |

FOREIGN PATENT DOCUMENTS

| | | |
|---|---|---|
| EP | 0486280 | 11/1991 |
| EP | 0640594 A1 | 3/1995 |
| EP | 0709375 | 10/1995 |
| EP | 1191024 | 3/2002 |
| EP | 1117616 | 4/2003 |
| EP | 02 74 1724 | 3/2004 |
| WO | WO 95/14025 | 11/1994 |
| WO | WO 96/27583 | 9/1996 |
| WO | WO 1996/27583 | 9/1996 |
| WO | WO 98/50359 | 5/1998 |
| WO | WO 99/06361 | 2/1999 |
| WO | WO 99/42443 | 2/1999 |
| WO | WO 99/24399 | 5/1999 |
| WO | WO 00/09103 | 8/1999 |
| WO | WO 00/35886 | 12/1999 |
| WO | WO 00/12477 | 3/2000 |
| WO | WO 00/12478 | 3/2000 |
| WO | WO 00/40577 | 7/2000 |
| WO | WO 00/75106 | 12/2000 |
| WO | WO 01/05756 | 1/2001 |
| WO | WO 01/12189 | 2/2001 |
| WO | WO 01/22363 | 3/2001 |
| WO | WO 01/34573 | 5/2001 |
| WO | WO 02/006232 | 1/2002 |
| WO | WO 02/014262 | 2/2002 |
| WO | WO 02/014354 | 2/2002 |
| WO | WO 02/020515 | 3/2002 |
| WO | WO 02/074749 | 9/2002 |
| WO | WO 02/074751 | 9/2002 |
| WO | WO 02/074752 | 9/2002 |
| WO | WO 02/074767 | 9/2002 |
| WO | WO 02074748 | 9/2002 |
| WO | WO 02074750 | 9/2002 |
| WO | WO 02/96426 | 12/2002 |
| WO | WO 03/040098 | 5/2003 |
| WO | WO 2004/020415 | 3/2004 |
| WO | WO 2004/024060 | 3/2004 |
| WO | WO 2004/024698 | 3/2004 |
| WO | WO 2004/024715 | 3/2004 |
| WO | WO 2004/024718 | 3/2004 |
| WO | WO 2004/024721 | 3/2004 |

OTHER PUBLICATIONS

Michaelides et al., "Recent Advances in Matrix Metalloproteinase Inhibitors Research", *Current Pharmaceutical Design* 5:787-819 (1999).

Mock et al., "Principles of Hydroxamate Inhibition of Metalloproteases: Carboxypeptides A", *Biochemistry* 39:13945-13952 (2000).

Aharony et al. "Pharmacological Characterization of a New Class of Nonpeptide Neurokinin A Antagonists that Demonstrate Species Selectivity." J. Pharmacol. Exp. Ther. 274:3 (1995), pp. 1216-1221.

Aimoto et al. "Synthesis of Carriers of Differing Strokes Radius with Activated Acyl Groups for Use as Reagents in Labeling Membrane Proteins." Journal of Biological Chemistry, vol. 256(10), pp. 5134-5143, 1981.

Chemical Abstracts, vol. 65, 1966, ABSTRACT No. 13684 h, M. Lora-Tamayo et al.: "Potential anticancer agents. I. Glutamine sulfonate analogs", & Anales Real Soc. Espan. Fis. Quim (Madrid), Ser. B. 62(2), 173-86.

Croce, P. et al. "Stereoselective aldol addition of a chirai glycine enloate synthon to heteroaromatic aldehydes." Heterocycles, 52:3 (2000) pp. 1337-1344.

Knabe, J. "Razemate und enantiomere basisch substituierter 5-phenylhydantoine." Pharmazie. 52:12 (1997) pp. 912-919.

Bright et al. "Monoclonal Antibodies as Surrogate Receptors in High Throughput Screen for Compounds that Enhance Insulin Sensitivity." Life Sciences. 61:23 (1997), pp. 2305-2315.

Lora-Tamayo et al. "anticancerousos Potenciales." An. Quim. 64:6 (1968), pp. 591-606.

Miyake, Toshiaki et al. "Studies on Glycosylation of erythro-Beta-Hydroxy-L-histidine. A Key Step of Blemycin Total Synthesis." Bull. Chem. Soc. Jpn. 59 (1986), pp. 1387-1395.

Nakajima, Riichiro et al. "The utility of 4-(2-thienyl)pyridines as a derivatization reagent for hplc and ce." Analytical Sciences. 7, Supplement 1991, pp. 177-180.

Nicolet, Ben. "Interpretation of the Dyhydration of Acetylglutamic acid by Means of Glutamylthiohydantoin Derivatives." Journal of the American Chemical Society, 1930, pp. 1192-1195.

Owa, Takashi et al. "Man-Designed Bleomycins: Significance of the binding Sites as Enzyme Models and of the Stereochemistry of the Linker Moiety." Tetrahedron. 48:7 (1992) pp. 1193-1208.

Peng, Sean X. "Separation and identification of methods for metalloproteinase inhibitors." Journal of Chromatography B. 764 (2001), pp. 59-80.

Saito, Sei-ichi et al. "A new synthesis of deglyco-bleomycine A2 aiming at the total synthesis of bleomycin." Tetrahedron Letters. 23(5) (1982), pp. 529-532.

STN International, file CAPLUS, accession No. 1978:424767, Raulais, Daniel J.P., "Synthesis and characterization of phenylthiohydantoin derivatives of amino-acids protected in their sid-chain functions, and their application for monitoring olid-phase peptide synthesis," & Journal of Chemical Research, Synopses (1978), p. 11.

STN International, file CAPLUS, accession No. 1994:299315, Document No. 120:299315, Sakamoto, Shuichi et al., "Preparation of pyridylserine derivatives as psychotropics," WO, A1, 9320053, 1931014, See CAS RN 154696-31-8, 154697-48-0.

STN International, file CAPLUS, accession No. 1997:644516, Batty, Craig et al. "Synthesis and exchange reaction of 5-alkyl-2oxo-6-thioxo-1,2,3,6-hexahydropyrimidine-4-carboxylic acids" & Journal of Heterocyclic Chemistry (1997), 34:3, 1355-1367.

STN International, file CAPLUS, accession No. 2002:640897, Gooding, Owen W. et al. "Use of Statistical Design of Experiments in the Optimization of Amide Synthesis Utilizing Polystryene-Supported N-Hydroxybenzotriazole Resin" & Journal of Combinatorial Chemistry (2002), 4(6), 576-583.

STN International, File CAPLUS, CAPLUS accession No. 1968:506154, Doc. No. 69:106154, Lora-Tamayo, J. et al.: "Potential anticancer agents, VI. Sulfonic analogs of aspartic acid", & An. Quim. (1968), 64(6), 591-606.

STN International, File CAPLUS, CAPLUS accession No. 1974:463633, Doc. No. 81:63633, Blaha, Ludvik et al.: "5-Methyl-5-phenoxymethyl-hydantoins", & CS 151744, B, 19731119.

STN International, File CAPLUS, CAPLUS accession No. 1988:631020, Doc. No. 109:231020, Mitsui Toatsu Chemicals, Inc.: "Process for the preparation of 5-benzylhydantoins as intermediates for aromatic amino acids": & JP, A2, 63079879, 19880409.

STN International, File CAPLUS, CAPLUS accession No. 1989:173366, Doc. No. 110:173366, Oh, Chang Hyun et al., "Synthesis of new hydantoin-3-acetic acid derivatives", & Bull. Korean Chem. Soc. (1988), 9(4), 231-5.

STN International, File CAPLUS, CAPLUS accession No. 1990:138955, Doc. No. 112:138955, Crooks, Peter A. et al.: "Synthesis of 5-benzoyl-5-phenyl-and-5-(Phenylhydroxymethyl)-5-phenylhydantoins as potential anticonvulsants"; & J. Heterocycl. Chem. (1989), 26(4), 1113-17.

Whittaker et al. "Design and Therapeutic Application of Matrix Metalloproteinase Inhibitors." Chem Rev. 99 (1999), pp. 2735-2776.

* cited by examiner

METALLOPROTEINASE INHIBITORS

CROSS-REFERENCE TO RELATED APPLICATIONS

This application is the national phase application under 35 U.S.C. § 371 of PCT International Application No. PCT/SE02/02023, which has an international filing date of Nov. 6, 2002, and which claims priority to Swedish Application Serial No. 0103710-0, filed Nov. 7, 2001. The contents of the applications are incorporated by reference in their entirety.

The present invention relates to compounds useful in the inhibition of metalloproteinases and in particular to pharmaceutical compositions comprising these, as well as their use.

The compounds of this invention are inhibitors of one or more metalloproteinase enzymes. Metalloproteinases are a superfamily of proteinases (enzymes) whose numbers in recent years have increased dramatically. Based on structural and functional considerations these enzymes have been classified into families and subfamilies as described in N. M. Hooper (1994) FEBS Letters 354:1–6. Examples of metalloproteinases include the matrix metalloproteinases (MMP) such as the collagenases (MMP1, MMP8, MMP13), the gelatinases (MMP2, MMP9), the stromelysins (MMP3, MMP10, MMP11), matrilysin (MMP7), metalloelastase (MMP12), enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265–279).

Metalloproteinases have been associated with many disease conditions. Inhibition of the activity of one or more metalloproteinases may well be of benefit in these disease conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atheroscelerosis; asthma; rhinitis; and chronic obstructive pulmonary diseases (COPD).

MMP12, also known as macrophage elastase or metalloelastase, was initially cloned in the mouse by Shapiro et al (1992, Journal of Biological Chemistry 267: 4664) and in man by the same group in 1995. MMP-12 is preferentially expressed in activated macrophages, and has been shown to be secreted from alveolar macrophages from smokers (Shapiro et al, 1993, Journal of Biological Chemistry, 268: 23824) as well as in foam cells in atherosclerotic lesions (Matsumoto et al, 1998, Am J Pathol 153: 109). A mouse model of COPD is based on challenge of mice with cigarette smoke for six months, two cigarettes a day six days a week. Wildtype mice developed pulmonary emphysema after this treatment. When MMP12 knock-out mice were tested in this model they developed no significant emphysema, strongly indicating that MMP-12 is a key enzyme in the COPD pathogenesis. The role of MMPs such as MMP12 in COPD (emphysema and bronchitis) is discussed in Anderson and Shinagawa, 1999, Current Opinion in Anti-inflammatory and Immunomodulatory Investigational Drugs 1(1): 29–38. It was recently discovered that smoking increases macrophage infiltration and macrophage-derived MMP-12 expression in human carotid artery plaques Kangavari (Matetzky S, Fishbein M C et al., Circulation 102:(18), 36–39 Suppl. S, Oct. 31, 2000).

MMP13, or collagenase 3, was initially cloned from a cDNA library derived from a breast tumour [J. M. P. Freije et al. (1994) Journal of Biological Chemistry 269(24): 16766–16773]. PCR-RNA analysis of RNAs from a wide range of tissues indicated that MMP13 expression was limited to breast carcinomas as it was not found in breast fibroadenomas, normal or resting mammary gland, placenta, liver, ovary, uterus, prostate or parotid gland or in breast cancer cell lines (T47-D, MCF-7 and ZR75-1). Subsequent to this observation MMP13 has been detected in transformed epidermal keratinocytes [N. Johansson et al., (1997) Cell Growth Differ. 8(2):243–250], squamous cell carcinomas [N. Johansson et al., (1997) Am. J. Pathol. 151(2):499–508] and epidermal tumours [K. Airola et al., (1997) J. Invest. Dermatol. 109(2):225–231]. These results are suggestive that MMP13 is secreted by transformed epithelial cells and may be involved in the extracellular matrix degradation and cell-matrix interaction associated with metastasis especially as observed in invasive breast cancer lesions and in malignant epithelia growth in skin carcinogenesis.

Recent published data implies that MMP13 plays a role in the turnover of other connective tissues. For instance, consistent with MMP13's substrate specificity and preference for degrading type II collagen [P. G. Mitchell et al., (1996) J. Clin. Invest. 97(3):761–768; V. Knauper et al., (1996) The Biochemical Journal 271:1544–1550], MMP13 has been hypothesised to serve a role during primary ossification and skeletal remodelling [M. Stahle-Backdahl et al., (1997) Lab. Invest. 76(5):717–728; N. Johansson et al., (1997) Dev. Dyn. 208(3):387–397], in destructive joint diseases such as rheumatoid and osteo-arthritis [D. Wernicke et al., (1996) J. Rheumatol. 23:590–595; P. G. Mitchell et al., (1996) J. Clin. Invest. 97(3):761–768; O. Lindy et al., (1997) Arthritis Rheum 40(8):1391–1399]; and during the aseptic loosening of hip replacements [S. Imai et al., (1998) J. Bone Joint Surg. Br. 80(4):701–710]. MMP13 has also been implicated in chronic adult periodontitis as it has been localised to the epithelium of chronically inflamed mucosa human gingival tissue [V. J. Uitto et al., (1998) Am. J. Pathol 152(6): 1489–1499] and in remodelling of the collagenous matrix in chronic wounds [M. Vaalamo et al., (1997) J. Invest. Dermatol. 109(1):96–101].

MMP9 (Gelatinase B; 92 kDa TypeIV Collagenase; 92 kDa Gelatinase) is a secreted protein which was first purified, then cloned and sequenced, in 1989 [S. M. Wilhelm et al (1989) J. Biol Chem. 264 (29): 17213–17221; published erratum in J. Biol Chem. (1990) 265 (36): 22570]. A recent review of MMP9 provides an excellent source for detailed information and references on this protease: T. H. Vu & Z. Werb (1998) (In: Matrix Metalloproteinases. 1998. Edited by W. C. Parks & R. P. Mecham. pp 115–148. Academic Press. ISBN 0-12-545090-7). The following points are drawn from that review by T. H. Vu & Z. Werb (1998).

The expression of MMP9 is restricted normally to a few cell types, including trophoblasts, osteoclasts, neutrophils and macrophages. However, it's expression can be induced in these same cells and in other cell types by several mediators, including exposure of the cells to growth factors or cytokines. These are the same mediators often implicated in initiating an inflammatory response. As with other secreted MMPs, MMP9 is released as an inactive Pro-enzyme which is subsequently cleaved to form the enzymatically active enzyme. The proteases required for this activation in vivo are not known. The balance of active MMP9 versus inactive enzyme is further regulated in vivo by interaction with TIMP-1 (Tissue Inhibitor of Metalloproteinases-1), a naturally-occurring protein. TIMP-1 binds to the C-terminal region of MMP9, leading to inhibition of the catalytic domain of MMP9. The balance of induced expression of ProMMP9, cleavage of Pro- to active MMP9 and the presence of TIMP-1 combine to determine the amount of catalytically active MMP9 which is present at a local site. Proteolytically active MMP9 attacks substrates which include gelatin, elastin, and native Type IV and Type V collagens; it has no activity against native Type I collagen, proteoglycans or laminins.

There has been a growing body of data implicating roles for MMP9 in various physiological and pathological processes. Physiological roles include the invasion of embryonic trophoblasts through the uterine epithelium in the early stages of embryonic implantation; some role in the growth and development of bones; and migration of inflammatory cells from the vasculature into tissues.

MMP-9 release, measured using enzyme immunoassay, was significantly enhanced in fluids and in AM supernatants from untreated asthmatics compared with those from other populations [Am. J. Resp. Cell & Mol. Biol., (Nov 1997) 17(5):583–591]. Also, increased MMP9 expression has been observed in certain other pathological conditions, thereby implicating MMP9 in disease processes such as arthritis, tumour metastasis, Alzheimer's, Multiple Sclerosis, and plaque rupture in atherosclerosis leading to acute coronary conditions such as Myocardial Infarction.

MMP-8 (collagenase-2, neutrophil collagenase) is a 53 kD enzyme of the matrix metalloproteinase family that is preferentially expressed in neutrophils. Later studies indicate MMP-8 is expressed also in other cells, such as osteoarthritic chondrocytes [Shlopov et al, (1997) Arthritis Rheum, 40:2065]. MMPs produced by neutrophils can cause tissue remodelling, and hence blocking MMP-8 should have a positive effect in fibrotic diseases of for instance the lung, and in degradative diseases like pulmonary emphysema. MMP-8 was also found to be up-regulated in osteoarthritis, indicating that blocking MMP-8 may also be beneficial in this disease.

MMP-3 (stromelysin-1) is a 53 kD enzyme of the matrix metalloproteinase enzyme family. MMP-3 activity has been demonstrated in fibroblasts isolated from inflamed gingiva [Uitto V. J. et al, (1981) J. Periodontal Res., 16:417–424], and enzyme levels have been correlated to the severity of gum disease [Overall C. M. et al, (1987) J. Periodontal Res., 22:81–88]. MMP-3 is also produced by basal keratinocytes in a variety of chronic ulcers [Saarialho-Kere U. K. et al, (1994) J. Clin. Invest., 94:79–88]. MMP-3 mRNA and protein were detected in basal keratinocytes adjacent to but distal from the wound edge in what probably represents the sites of proliferating epidermis. MMP-3 may thus prevent the epidermis from healing. Several investigators have demonstrated consistent elevation of MMP-3 in synovial fluids from rheumatoid and osteoarthritis patients as compared to controls [Walakovits L. A. et al, (1992) Arthritis Rheum., 35:35–42; Zafarullah M. et al, (1993)J. Rheumatol., 20:693–697]. These studies provided the basis for the belief that an inhibitor of MMP-3 will treat diseases involving disruption of extracellular matrix resulting in inflammation due to lymphocytic infiltration, or loss of structural integrity necessary for organ function.

A number of metalloproteinase inhibitor compounds are known and some are being developed for pharmaceutical uses (see for example the review of MMP inhibitors by Beckett R. P. and Whittaker M., 1998, Exp. Opin. Ther. Patents, 8(3):259–282). Different classes of compounds may have different degrees of potency and selectivity for inhibiting various metalloproteinases.

Whittaker M. et al (1999, Chemical Reviews 99(9): 2735–2776) review a wide range of known MMP inhibitor compounds. They state that an effective M inhibitor requires a zinc binding group or ZBG (functional group capable of chelating the active site zinc(II) ion), at least one functional group which provides a hydrogen bond interaction with the enzyme backbone, and one or more side chains which undergo effective van der Waals interactions with the enzyme subsites. Zinc binding groups in known MMP inhibitors include hydroxamates, reverse hydroxamates, thiols, carboxylates and phosphonic acids.

We have now discovered a new class of compounds that are metalloproteinase inhibitors and are of particular interest in inhibiting MMPs. The compounds of the invention are potent MMP12 inhibitors and have beneficial potency, selectivity and/or pharmacokinetic properties.

A metalloproteinase inhibitor is a compound that inhibits the activity of a metalloproteinase enzyme (for example, an MMP). By way of non-limiting example the inhibitor compound may show IC50s in vitro in the range of 0.1–1000 nanomolar.

In a first aspect of the invention we now provide a compound of the formula I

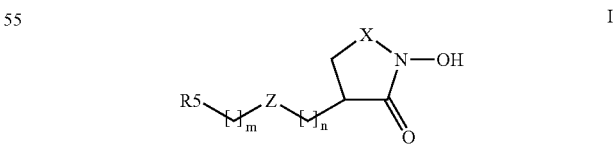

wherein
X is selected from CO, CS or CR1R2;
Z is selected from SO2, SO2N(R3), N(R4)SO2, or N(R4)SO2N(R3);
n is 0 or 1;
m is 0 or 1;

R1 and R2 are each independently selected from H or C1–6 alkyl;

R3 and R4 are each independently selected from H, C1–6 alkyl, phenyl-1-C6 alkyl, or heteroaryl-C1–6 alkyl;

R5 is a mono-, di- or tricyclic group comprising one, two or three ring structures each of up to 7 ring atoms independently selected from cycloalkyl, aryl, heterocycloalkyl or heteroaryl, with each ring structure being independently optionally substituted by one or more substituents independently selected from halogen, C1–6 alkyl, C1–6 alkenyl, C1–6 haloalkyl, C1–6 alkoxy, C1–6 haloalkoxy, thiolo, C1–6 thioloalkyl, C1–6 thiolo-haloalkyl, sulfono, C1–6 sulfonoalkyl, C1–6 sulfono-haloalkyl, aminosulfonyl, sulfoxy, C1–6 sulfoxyalkyl, amino, cyanoamino, hydrazine, C1–6 aminoalkyl, aminocarbonylamine, methylsulfonamine, acetamido, N—(C1–3 alkyl)acetamido, carboxamide, N(C1–3 alkyl)carboxamide, N,N -di-(C1–3 alkyl)carbamate, cyano, C1–6 cyanoalkyl, hydroxy, nitro, nitroso, formyl, N-methylformamide, methylformate, ethylformate, acetyl, acetoxy;

when R5 is a di- or tricyclic group, each ring structure is joined to the next ring structure by a direct bond, by —O—, by —S—, by —N—, by C1–3 alkyl, by C1–3 heteroalkyl, or is fused to the next ring structure;

Any alkyl groups outlined above may be straight chain or branched;

Any heteroalkyl group outlined above is a heteroatom-substituted alkyl containing one or more heteroatoms independently selected from N, O, S;

Any heterocycloalkyl or heteroaryl group outlined above contains one or more heteroatoms independently selected from N, O, S.

Within R5, each optional substituent on a ring structure is selected from: Halogen (for example fluorine, chlorine, bromine, or iodine); C1–6 alkyl (for example methyl, ethyl, propyl, isopropyl, butyl, or tert-butyl); C1–6 alkenyl (for example vinyl); C1–6 haloalkyl (for example trifluoromethyl, pentafluoroethyl); C1–6 alkoxy (for example methoxy, ethoxy, isopropoxy, butoxy, tertbutoxy, hydroxymethyl, methoxymethyl); C1–6 haloalkoxy (for example trifluoromethoxy); Thiolo (—SH); C1–6 thioloalkyl (for example methylsulfide, ethylsulfide, propylsulfide); C1–6 thiolo-haloalkyl (for example trifluoromethylsulfide); Sulfono; C1–6 sulfonoalkyl (for example methylsulfonyl, ethylsulfonyl); C1–6 sulfono-haloalkyl (for example trifluoromethylsulfonyl); Aminosulfonyl; Sulfoxy; C1–6 sulfoxyalkyl (for example methylsulfoxy); Amino; Cyanoamino; Hydrazine; C1–6 aminoalkyl (for example methylamine, ethylamine, propylamine, butylamine, dimethylamine, diethylamine, formylamine); Aminocarbonylamine; Methylsulfonamine; Acetamido (—CH2CONH2 or —NHCOCH3); N—(C1–3 alkyl)acetamido; Carboxamide (for example ethyloxycarbonylamine); N(C1–3 alkyl)carboxamide; N,N -di-(C1–3 alkyl)carbamate; Cyano; C1–6 cyanoalkyl (for example cyanomethyl); Hydroxy; Nitro; Nitroso; Formyl; N-methylformamide; Methylformate; Ethylformate; Acetyl; Acetoxy.

Preferably R5 is a mono-, di- or tricyclic group comprising one, two or three ring structures each of up to 7 ring atoms independently selected from cycloalkyl, aryl, heterocycloalkyl or heteroaryl, with each ring structure being independently optionally substituted by one or more substituents independently selected from halogen, C1–6 alkyl, C1–6 haloalkyl, C1–6 alkoxy, C1–6 haloalkoxy, acetamido, N—(C1–3 alkyl)acetamido, carboxamide, N(C1–3 alkyl) carboxamide, N,N -di-(C1–3 alkyl)carbamate or cyano.

Suitable values for R5 include the following:

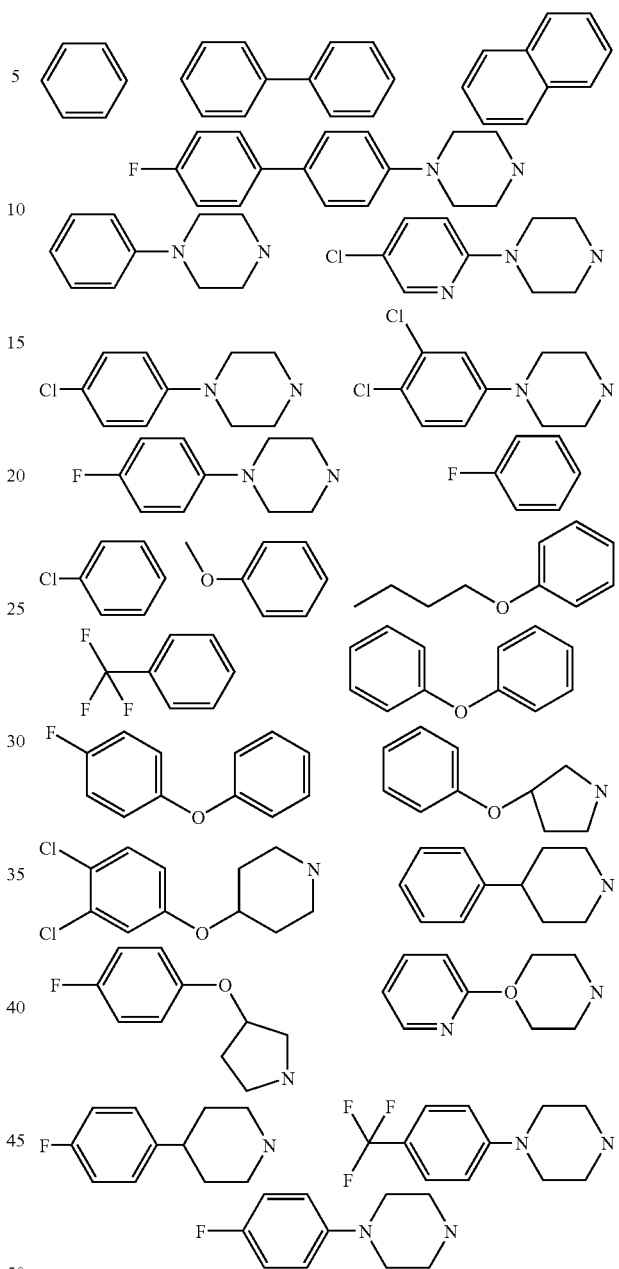

Preferred compounds of the formula I are those wherein any one or more of the following apply:

X is CO or CH2;

Z is SO2 or SO2N(R3);

m and n are each 0;

R3 is H, C1–6 alkyl, or phenyl-C1–6 alkyl;

R5 is a dicyclic or tricyclic group comprising one or two ring structures each of up to 7 ring atoms independently selected from aryl or heterocycloalkyl, with each ring structure being independently optionally substituted by one or two substituents independently selected from halogen, C1–6 alkyl, C1–6 haloalkyl, C1–6 alkoxy, C1–6 haloalkoxy; preferably at least one ring structure is substituted; most preferably both ring structures are substituted.

Most preferred compounds of the invention are those of formula II

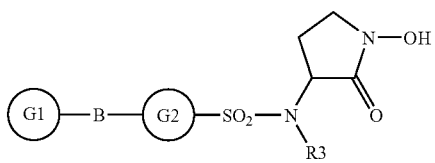

wherein
R3 is selected from H, C1–6 alkyl or phenyl-C1–6 alkyl;
each of G1 and G2 is a monocyclic group, each comprising one ring structure of up to 7 ring atoms independently selected from cycloalkyl, aryl, heterocycloalkyl or heteroaryl, with each ring structure being independently optionally substituted by one or two substituents independently selected from halogen, C1–6 alkyl, C1–6 haloalkyl, C1–6 alkoxy, or C1–6 haloalkoxy;
B is a direct bond or —O—;
Any alkyl groups outlined above may be straight chain or branched;
Any heteroalkyl group outlined above is a heteroatom-substituted alkyl containing one or more heteroatoms independently selected from N, O, S;
Any heterocycloalkyl or heteroaryl group outlined above contains one or more heteroatoms independently selected from N, O, S.

Preferred compounds of the formula II are those wherein any one or more of the following apply:
G1 is an aryl or heteroaryl ring structure (preferably phenyl), optionally substituted by halogen or C1–3 haloalkyl; G2 is an aryl or heteroaryl ring structure (preferably phenyl), or
G2 is a 5- or 6-membered heterocycloalkyl ring structure containing one or two nitrogen atoms;
B is a direct bond.

It will be appreciated that the particular substituents and number of substituents in compounds of formulae I or II are selected so as to avoid sterically undesirable combinations.

Each exemplified compound represents a particular and independent aspect of the invention.

Where optically active centres exist in the compounds of formulae I or II, we disclose all individual optically active forms and combinations of these as individual specific embodiments of the invention, as well as their corresponding racemates. Racemates may be separated into individual optically active forms using known procedures (cf. Advanced Organic Chemistry: 3rd Edition: author J March, p104–107) including for example the formation of diastereomeric derivatives having convenient optically active auxiliary species followed by separation and then cleavage of the auxiliary species.

It will be appreciated that the compounds according to the invention may contain one or more asymmetrically substituted carbon atoms. The presence of one or more of these asymmetric centres (chiral centres) in a compound of formulae I or II can give rise to stereoisomers, and in each case the invention is to be understood to extend to all such stereoisomers, including enantiomers and diastereomers, and mixtures including racemic mixtures thereof.

Where tautomers exist in the compounds of formulae I or II, we disclose all individual tautomeric forms and combinations of these as individual specific embodiments of the invention.

As previously outlined the compounds of the invention are metalloproteinase inhibitors, in particular they are inhibitors of MMP12. Each of the above indications for the compounds of the formulae I or II represents an independent and particular embodiment of the invention.

Certain compounds of the invention are of particular use as inhibitors of MMP13 and/or MMP9 and/or MMP8 and/or MMP3. Certain compounds of the invention are of particular use as aggrecanase inhibitors ie. inhibitors of aggrecan degradation.

Compounds of the invention show a favourable selectivity profile. Whilst we do not wish to be bound by theoretical considerations, the compounds of the invention are believed to show selective inhibition for any one of the above indications relative to any MMP1 inhibitory activity, by way of non-limiting example they may show 100–1000 fold selectivity over any MMP1 inhibitory activity.

The compounds of the invention may be provided as pharmaceutically acceptable salts. These include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

The compounds of the invention may also be provided as pharmaceutically acceptable carbamates or amides.

They may also be provided as in vivo hydrolysable esters. These are pharmaceutically acceptable esters that hydrolyse in the human body to produce the parent compound. Such esters can be identified by administering, for example intravenously to a test animal, the compound under test and subsequently examining the test animal's body fluids. Suitable in vivo hydrolysable esters for carboxy include methoxymethyl and for hydroxy include formyl and acetyl, especially acetyl. Other suitable esters include carbonic esters.

In order to use a compound of the formulae I or II or a pharmaceutically acceptable salt or in vivo hydrolysable ester thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formulae I or II or a pharmaceutically acceptable salt or an in vivo hydrolysable ester thereof and a pharmaceutically acceptable carrier.

The pharmaceutical compositions of this invention may be administered in standard manner for the disease condition that it is desired to treat, for example by oral, topical, parenteral, buccal, nasal, vaginal or rectal adminstration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to hereinabove.

The pharmaceutical compositions of this invention will normally be administered to humans so that, for example, a daily dose of 0.5 to 75 mg/kg body weight (and preferably of 0.5 to 30 mg/kg body weight is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention.

Therefore in a further aspect, the present invention provides a compound of the formulae I or II or a pharmaceutically acceptable salt or in vivo hydrolysable ester thereof for use in a method of therapeutic treatment of the human or animal body or for use as a therapeutic agent. In particular we disclose use in the treatment of a disease or condition mediated by MMP12 and/or MMP13 and/or MMP9 and/or MMP8 and/or MMP3 and/or aggrecanase; especially use in the treatment of a disease or condition mediated by MMP12.

related diseases such as Alzheimer's and Multiple Sclerosis (MS), hematological disorders.

Preparation of the Compounds of the Invention

In another aspect the present invention provides processes for preparing a compound of the formulae I or II or a pharmaceutically acceptable salt or in vivo hydrolysable ester thereof which processes are described below.

The invention provides a process for preparing a compound of the formula Ia or a pharmaceutically acceptable salt or in vivo hydrolysable ester thereof which process comprises converting an N-protected aminodicarboxylic acid of the formula Va to an anhydride of the formula IVa by the action of a carboxylate activating agent, reacting the anhydride of formula IVa with an O-protected hydroxylamine of the formula R"ONH2 to produce an N-alkoxy compound of the formula IIIa, converting to an amine of the formula IIa followed by deprotection to form a compound of the formula Ia, all as set out below, and optionally thereafter forming a pharmaceutically acceptable salt or in vivo hydrolysable ester of the compound of formula Ia:

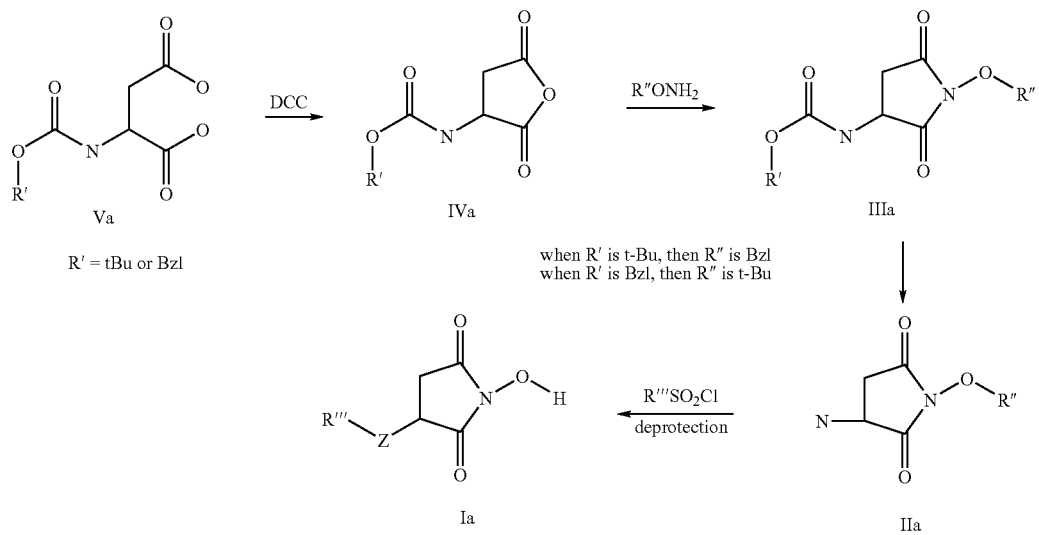

In yet a further aspect the present invention provides a method of treating a metalloproteinase mediated disease condition which comprises administering to a warm-blooded animal a therapeutically effective amount of a compound of the formulae I or II or a pharmaceutically acceptable salt or in vivo hydrolysable ester thereof.

We also disclose the use of a compound of the formulae I or II or a pharmaceutically acceptable salt or in vivo hydrolysable precursor thereof in the preparation of a medicament for use in the treatment of a disease condition mediated by one or more metalloproteinase enzymes.

Metalloproteinase mediated disease conditions include asthma, rhinitis, chronic obstructive pulmonary diseases (COPD), arthritis (such as rheumatoid arthritis and osteoarthritis), atherosclerosis and restenosis, cancer, invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS wherein
Z is SO2N(R3);
R3 is H;
R''' is [CH2]$_m$R5, and m and R5 are as hereinbefore described for the compound of formula I;
t-bu is t-butyl; Bzl is benzyl.

Compounds of the formula Va contain the protecting group R'. Convenient starting materials of formula Va include all stereoisomers of t-butyl or benzyl carbamates of aminodicarboxylic acids like α-aspartic acids derivatives. It will be appreciated that other N-protecting groups and sources of aminodicarboxylic acids may be used.

To convert the dicarboxylic acids of formula Va to anhydrides of formula IVa, suitable carboxylate activating agents include carbodiimides, acyl chlorides, phosphoryl chlorides or alkyl chloroformiates. Preferably, carbodiimides like dicyclohexylcarbodiimide or diisopropylcarbodiimide or BOP-Cl (bis-(2-oxazolidinon-1-yl)phosphoryloxychloride) in dichloromethane or tetrahydrofurane are used.

Compounds of the formula R"ONH2 (O-protected hydroxylamines) contain the protecting group R", where R"

is not of similar reactivity as R' due the need remove R' and R" independantly at a later stage in the process. Preferably, O-protected hydroxylamines where R" is t-butyl, benzyl, 4-methoxybenzyl and t-butyldimethylsilyl are heated with compounds of formula IVa in aromatic solvents like benzene, toluene or xylenes at 80° C. to reflux temperature for 5–24 h to produce N-alkoxy compounds of formula IIIa. The protecting group R' is then removed to produce the amines of formula IIa as the free bases or the corresponding salts. The choice of reaction conditions to remove R' is evident to those skilled in the art. Subsequent reaction of the amines of formula IIa with sulfonyl chlorides or sulfamoyl chlorides R'''SO$_2$Cl, (preparation of new sulfamoyl chlorides is described in the Examples), preferably in the presence of sterically hindered bases like triethyl amine, diisopropylethyl amine, lutidine etc, in aprotic polar solvents such as dichloromethane, tetrahydrofurane or dimethylformamide at 20–80° C. or heated by repeated (2–20×) bursts (5–20 s) of microvave energy (50–250 W) in a sealed vessel, followed by deprotection by standard methods such as catalytic hydrogenation or action of acids like trifluoroacetic acid, yields compounds of formula Ia.

In another aspect the present invention provides a process for preparing a compound of the formula Ib or a pharmaceutically acceptable salt or in vivo hydrolysable ester thereof which process comprises acylating or sulfonylating a homoserine lactone of the formula Vb to form a compound of the formula IVb, hydroxylaminolysis to form a compound of the formula IIIb, conversion to a N-alkoxy lactam of formula IIb, optional treatment with an alkylating agent of the formula R4-halogen or R4-sulfonate ester, and deprotection to form a compound of the formula Ib, as set out below, and optionally thereafter forming a pharmaceutically acceptable salt or in vivo hydrolysable ester of the compound of formula Ib:

J. et al, 1989, J. Chem. Soc., Chem. Commun. 22: 1740–2; Leeson, P. D. and Williams, B. J., European patent number 318091) are sulfonylated by standard methods, followed by hydroxylaminolysis of the resulting lactone derivative of formula IVb, preferably with the aluminate formed from the hydroxylamine hydrochloride and trimethylaluminium in aromatic solvents such as benzene and toluene at reflux temperature, to produce the hydroxamic acid derivative IIIb. Conversion of compounds of formula IIIb to the N-alkoxy lactams of formula IIb is possible through activation of the hydroxyl as a sulfonate ester or via conversion to the halide followed by treatment with base, or subjecting the alcohols of formula IIIb to the Mitsonobu conditions. Preferably, conversion to the chloride by the action of triphenylphosphine and carbon tetrachloride and subsequent treatment with sodium hydride in dichlorometane at ambient temperature for 2–24 h yields compounds of formula IIb. Another preferred procedure is to treat the alcohols IIIb with triphenyl phosphine and diethyldiazodicarboxylate in tetrahydrofurane (Mitsonobu) at −20 to 0° C. for 2–24 h. The N-alkoxy lactams of formula IIb thus prepared can optionally be treated with alkylating agents R4-halogen or R4-sulfonate ester (R4 is as hereinbefore described) before deprotection (removal of R') by standard methods to yield compounds of formula Ib.

In another aspect the present invention provides a process for preparing a compound of the formula Ic or a pharmaceutically acceptable salt or in vivo hydrolysable ester thereof which process comprises acylating or sulfonylating a compound of the formula IIIc to form a compound of the formula IIc, optional alkylation and deprotection to form a compound of the formula Ic, as set out below, and optionally thereafter forming a pharmaceutically acceptable salt or in vivo hydrolysable ester of the compound of formula Ic:

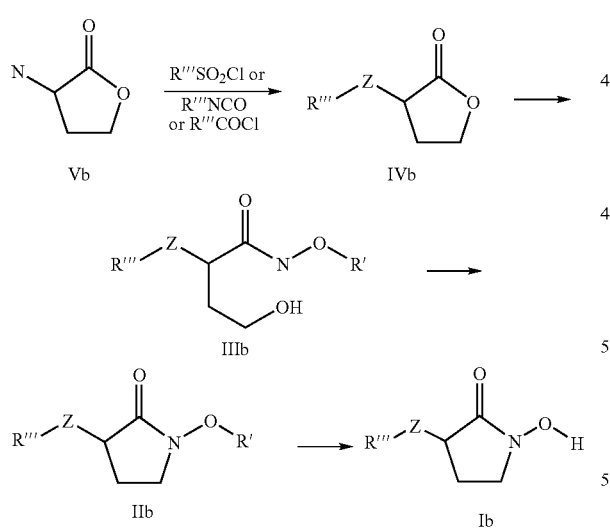

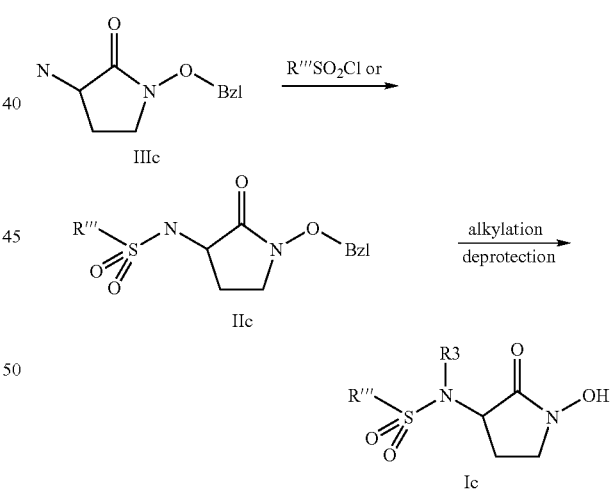

wherein
Z is SO2N(R3);
R3 is as hereinbefore described for the compound of formula I;
R''' is [CH2]$_m$R5, and m and R5 are as hereinbefore described for the compound of formula I.

Homoserine lactones of formula Vb (Flanagan, D. M. and Martin, L. L., 1992, U.S. Pat. No. 5,153,193); Williams, B.

wherein
R3 is as hereinbefore described for the compound of formula I;
R''' is [CH2]$_m$R5, and m and R5 are as hereinbefore described for the compound of formula I;
Bzl is benzyl.

Sulfonylation or acylation of compounds of formula IIIc by standard methods produces compounds of formula IIc. These can optionally be alkylated by alkyl halides (R3-halogen) such as methyl iodide, isopropy iodide, benzyl bromide, 3-pyridylmethyl chloride etc under standard basic conditions, or under Mitsonoby conditions (diazocarbonates, phoshines) with alcolhols (R3-OH), before deprotection by standard methods to form compounds of formula Ic.

In another aspect the present invention provides a process for preparing a compound of the formula Id or a pharmaceutically acceptable salt or in vivo hydrolysable ester thereof which process comprises acylating or sulfonylating a compound of the formula IIId to form a compound of the formula IId, optional alkylation and deprotection to form a compound of the formula Id, as set out below, and optionally thereafter forming a pharmaceutically acceptable salt or in vivo hydrolysable ester of the compound of formula Id. Compounds of formula IIId can be prepared from protected homoserine derivatives where Ptg and R are preferrably stable in acidic medium:

Bzl is benzyl.

Aldoximes of formula IVd are conveniently prepared from protected homoserine derivatives Vd. Reductive addition of alkyl radicals to compounds of formula IVd give benzyloxyamino intermediates which spontaneously form the corresponding lactam derivatives upon work-up or mild basic treatment. Alternatively, the aldoximes IVd (R2=H) are reduced to the corresponding benzyloxyamino intermediates. Subsequent deprotection of the amino group then yield amino lactam derivatives IIId. Sulfonylation of compounds of formula IIId by standard methods produces compounds of formula IId. These can optionally be alkylated by alkyl halides (R3-halide) such as methyl iodide, isopropy iodide, benzyl bromide, 3-pyridylmethyl chloride etc under standard basic conditions, or under Mitsonoby conditions (diazocarbonates, phoshines) with alcohols (R3-OH), before deprotection by standard methods to form compounds of formula Id.

In another aspect the present invention provides a process for preparing a compound of the formula Ie or a pharmaceutically acceptable salt or in vivo hydrolysable ester thereof which process comprises chlorine oxidation of compound of the formula Ve, followed by coupling of the formed sulfonyl chloride with amines to form a compound of the formula IVe, hydroxylaminolysis of wich gives protected hydroxamates of formula IIIe. Cyclization to compounds of formula IIe and deprotection to form a cyclic hydroxamic acid compound of the formula Ie, as set out below, and optionally thereafter forming a pharmaceutically acceptable salt or in vivo hydrolysable ester of the compound of formula Ie:

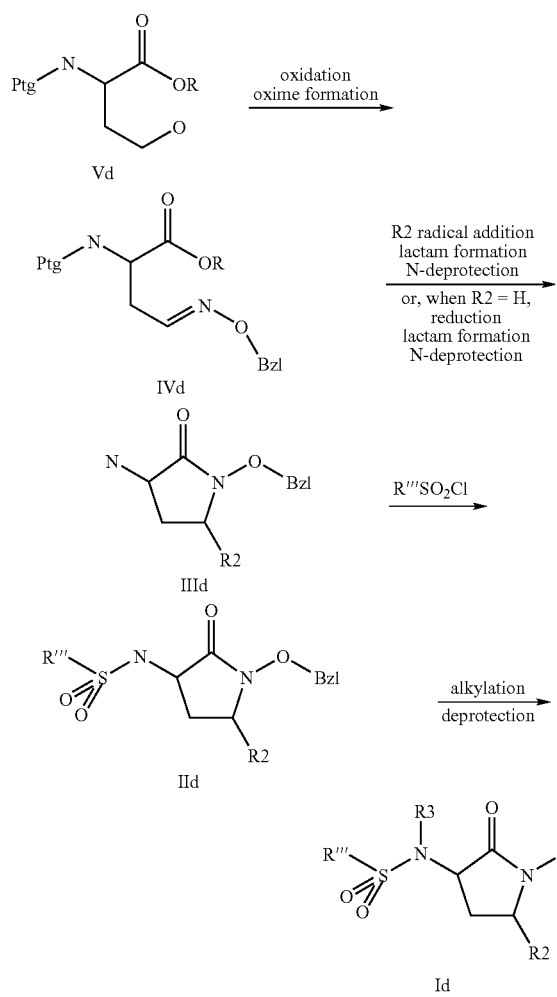

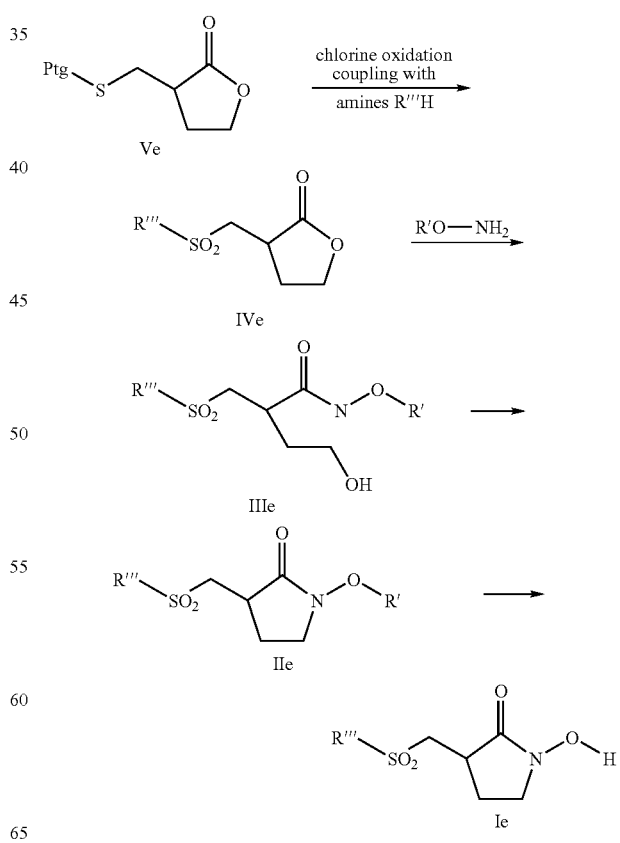

wherein

Ptg is a protecting group, preferrably Boc; when Ptg is the residue R'''SO$_2$, the step IIId to IId is omitted;

R is any alkyl or aryl group, preferrably methyl or ethyl;

R2 and R3 are as hereinbefore described for the compound of formula I;

R''' is [CH2]$_m$R5, and m and R5 are as hereinbefore described for the compound of formula I;

wherein

Ptg is a protecting group, preferably easily oxidized such as benzyl, isopropyl or an alkyl sulfide thus comprising(?) a disulfide in the Ptg-S bond.

R' is a protecting group, preferably t-butyl.

R''' is a primary or secondary amine, preferably a substituted cyclic secondary amine R5H. or a primary amine $NH_2[CH2]_mR5$, and m and R5 are as hereinbefore described for the compound of formula I;

Thus, sulfides of formula Ve are oxidized with chlorine preferably in water or water/acetic acid or water/dioxane, preferably cooled to 0–10° C. The sulfonyl chloride intermediates can be isolated or partially isolated by removal of volatiles under vacuum, followed by reaction with amines R'''H in aprotic solvents and bases, preferably THF or DMF and potassium carbonate or diethylisopropyl amine. Hydroxylaminolysis of the resulting lactone derivative of formula IVe, preferably with the aluminate formed from the hydroxylamine hydrochloride and trimethylaluminium in aromatic solvents such as benzene and toluene at reflux temperature, to produce the hydroxamic acid derivative IIIe. Conversion of compounds of formula IIIb to the N-alkoxy lactams of formula IIe is possible through activation of the hydroxyl as a sulfonate ester or via conversion to the halide followed by treatment with base, or subjecting the alcohols of formula IIIe to the Mitsonobu conditions. Preferably, conversion to the chloride by the action of triphenylphosphine and carbon tetrachloride and subsequent treatment with sodium hydride in dichlorometane at ambient temperature for 2–24 h yields compounds of formula IIe. Another preferred procedure is to treat the alcohols IIIe with triphenyl phosphine and diethyldiazodicarboxylate in tetrahydrofurane (Mitsonobu) at −20 to 0° C. for 2–24 h.

Alternatively, the order and conditions in the sequence Ive-Ie can be modified to allow greater ease of obtaining diversity in the R'''-portion: The sulfides of formula Ve (Ptg is Bzl) are oxidized to the sulfone (when R''' is still the Ptg of formula Ve) formula IVe by peroxide reagents such as hydrogen peroxide, Oxone™, MCPBA, then carried through the steps IVe to IIe to the corresponding N-alkoxy lactams. Chlorine oxidation to sulfonyl chlorides followed by coupling with amines and deprotection also furnishes compounds of formula Ie.

For all the processes described above, it will be appreciated that many of the relevant starting materials are commercially or otherwise available or may be synthesised by known methods or may be found in the scientific literature.

The compounds of the invention may be evaluated for example in the following assays:

Isolated Enzyme Assays

Matrix Metalloproteinase Family Including for Example MMP12. MMP13.

Recombinant human MMP12 catalytic domain may be expressed and purified as described by Parkar A. A. et al, (2000), Protein Expression and Purification, 20:152. The purified enzyme can be used to monitor inhibitors of activity as follows: MMP12 (50 ng/ml final concentration) is incubated for 30 minutes at RT in assay buffer (0.1M Tris-HCl, pH 7.3 containing 0.1M NaCl, 20 mM $CaCl_2$, 0.040 mM ZnCl and 0.05% (w/v) Brij 35) using the synthetic substrate Mca-Pro-Cha-Gly-Nva-His-Ala-Dpa-NH2 in the presence or absence of inhibitors. Activity is determined by measuring the fluorescence at $\lambda ex$ 328 nm and $\lambda em$ 393 nm. Percent inhibition is calculated as follows: % Inhibition is equal to the [$Fluorescence_{plus\ inhibitor}$−$Fluorescence_{background}$] divided by the [$Fluorescence_{minus\ inhibitor}$−$Fluorescence_{background}$].

Recombinant human proMMP13 may be expressed and purified as described by Knauper et al. [V. Knauper et al., (1996) The Biochemical Journal 271:1544–1550 (1996)]. The purified enzyme can be used to monitor inhibitors of activity as follows: purified proMMP13 is activated using 1 mM amino phenyl mercuric acid (APMA), 20 hours at 21° C.; the activated MMP13 (11.25 ng per assay) is incubated for 4–5 hours at 35° C. in assay buffer (0.1M Tris-HCl, pH 7.5 containing 0.1M NaCl, 20 mM CaCl2, 0.02 mM ZnCl and 0.05% (w/v) Brij 35) using the synthetic substrate 7-methoxycoumarin-4-yl)acetyl.Pro.Leu.Gly.Leu.N-3-(2,4-dinitrophenyl)-L-2,3-diaminopropionyl.Ala.Arg.$NH_2$ in the presence or absence of inhibitors. Activity is determined by measuring the fluorescence at $\lambda ex$ 328 nm and $\lambda em$ 393 nm. Percent inhibition is calculated as follows: % Inhibition is equal to the [$Fluorescence_{plus\ inhibitor}$−$Fluorescence_{background}$] divided by the [$Fluorescence_{minus\ inhibitor}$−$Fluorescence_{background}$].

A similar protocol can be used for other expressed and purified pro MMPs using substrates and buffers conditions optimal for the particular MMP, for instance as described in C. Graham Knight et al., (1992) FEBS Lett. 296(3):263–266.

Adamalysin Family Including for Example TNF Convertase

The ability of the compounds to inhibit proTNFα convertase enzyme may be assessed using a partially purified, isolated enzyme assay, the enzyme being obtained from the membranes of THP-1 as described by K. M. Mohler et al., (1994) Nature 370:218–220. The purified enzyme activity and inhibition thereof is determined by incubating the partially purified enzyme in the presence or absence of test compounds using the substrate 4',5'-Dimethoxy-fluoresceinyl Ser.Pro.Leu.Ala.Gln.Ala.Val.Arg.Ser.Ser.Ser.Arg.Cys (4-(3-succinimid-1-yl)-fluorescein)-$NH_2$ in assay buffer (50 mM Tris HCl, pH 7.4 containing 0.1% (w/v) Triton X-100 and 2 mM $CaCl_2$), at 26° C. for 18 hours. The amount of inhibition is determined as for MMP13 except $\lambda ex$ 490 nm and $\lambda em$ 530 nm were used. The substrate was synthesised as follows. The peptidic part of the substrate was assembled on Fmoc-NH-Rink-MBHA-polystyrene resin either manually or on an automated peptide synthesiser by standard methods involving the use of Fmoc-amino acids and O-benzotriazol-1-yl-N,N,N',N'-tetramethyluronium hexafluorophosphate (HBTU) as coupling agent with at least a 4- or 5-fold excess of Fmoc-amino acid and HBTU. $Ser^1$ and $Pro^2$ were double-coupled. The following side chain protection strategy was employed; $Ser^1$(But), $Gln^5$(Trityl), $Arg^{8,12}$ (Pmc or Pbf), $Ser^{9,10,11}$(Trityl), $Cys^{13}$(Trityl). Following assembly, the N-terminal Fmoc-protecting group was removed by treating the Fmoc-peptidyl-resin with in DMF. The amino-peptidyl-resin so obtained was acylated by treatment for 1.5–2 hr at 70° C. with 1.5–2 equivalents of 4',5'-dimethoxy-fluorescein-4(5)-carboxylic acid [Khanna & Ullman, (1980) Anal Biochem. 108:156–161) which had been preactivated with diisopropylcarbodiimide and 1-hydroxybenzotriazole in DMF]. The dimethoxyfluoresceinyl-peptide was then simultaneously deprotected and cleaved from the resin by treatment with trifluoroacetic acid containing 5% each of water and triethylsilane. The dimethoxyfluoresceinyl-peptide was isolated by evaporation, trituration with diethyl ether and filtration. The isolated peptide was reacted with 4-(N-maleimido)-fluorescein in DMF containing diisopropylethylamine, the product purified by RP- HPLC and finally isolated by freeze-drying from aqueous acetic acid. The product was characterised by MALDI-TOF MS and amino acid analysis.

Natural Substrates

The activity of the compounds of the invention as inhibitors of aggrecan degradation may be assayed using methods for example based on the disclosures of E. C. Arner et al., (1998) Osteoarthritis and Cartilage 6:214–228; (1999) Journal of Biological Chemistry, 274 (10), 6594–6601 and the antibodies described therein. The potency of compounds to act as inhibitors against collagenases can be determined as described by T. Cawston and A. Barrett (1979) Anal. Biochem. 99:340–345.

Inhibition of Metalloproteinase Activity in Cell/Tissue Based Activity

Test as an Agent to Inhibit Membrane Sheddases Such as TNF Convertase

The ability of the compounds of this invention to inhibit the cellular processing of TNFα production may be assessed in THP-1 cells using an ELISA to detect released TNF essentially as described K. M. Mohler et al., (1994) Nature 370:218–220. In a similar fashion the processing or shedding of other membrane molecules such as those described in N. M. Hooper et al., (1997) Biochem. J. 321:265–279 may be tested using appropriate cell lines and with suitable antibodies to detect the shed protein.

Test as an Agent to Inhibit Cell Based Invasion

The ability of the compound of this invention to inhibit the migration of cells in an invasion assay may be determined as described in A. Albini et al., (1987) Cancer Research 47:3239–3245.

Test as an Agent to Inhibit Whole Blood TNF Sheddase Activity

The ability of the compounds of this invention to inhibit TNFα production is assessed in a human whole blood assay where LPS is used to stimulate the release of TNFα. Heparinized (10 Units/ml) human blood obtained from volunteers is diluted 1:5 with medium (RPMI1640+bicarbonate, penicillin, streptomycin and glutamine) and incubated (160 µl) with 20 µl of test compound (triplicates), in DMSO or appropriate vehicle, for 30 min at 37° C. in a humidified (5% $CO_2$/95% air) incubator, prior to addition of 20 µl LPS (*E. coli*. 0111:B4; final concentration 10 µg/ml). Each assay includes controls of diluted blood incubated with medium alone (6 wells/plate) or a known TNFα inhibitor as standard. The plates are then incubated for 6 hours at 37° C. (humidified incubator), centrifuged (2000 rpm for 10 min; 4° C.), plasma harvested (50–100 µl) and stored in 96 well plates at −70° C. before subsequent analysis for TNFα concentration by ELISA.

Test as an Agent to Inhibit in Vitro Cartilage Degradation

The ability of the compounds of this invention to inhibit the degradation of the aggrecan or collagen components of cartilage can be assessed essentially as described by K. M. Bottomley et al., (1997) Biochem J. 323:483–488.

Pharmacodynamic Test

To evaluate the clearance properties and bioavailability of the compounds of this invention an ex vivo pharmacodynamic test is employed which utilises the synthetic substrate assays above or alternatively HPLC or Mass spectrometric analysis. This is a generic test which can be used to estimate the clearance rate of compounds across a range of species. Animals (e,g. rats, marmosets) are dosed iv or po with a soluble formulation of compound (such as 20% w/v DMSO, 60% w/v PEG400) and at subsequent time points (e.g. 5, 15, 30, 60, 120, 240, 480, 720, 1220 mins) the blood samples are taken from an appropriate vessel into 10 U heparin. Plasma fractions are obtained following centrifugation and the plasma proteins precipitated with acetonitrile (80% w/v final concentration). After 30 mins at −20° C. the plasma proteins are sedimented by centrifugation and the supernatant fraction is evaporated to dryness using a Savant speed vac. The sediment is reconstituted in assay buffer and subsequently analysed for compound content using the synthetic substrate assay. Briefly, a compound concentration-response curve is constructed for the compound undergoing evaluation. Serial dilutions of the reconstituted plasma extracts are assessed for activity and the amount of compound present in the original plasma sample is calculated using the concentration-response curve taking into account the total plasma dilution factor.

In Vivo Assessment

Test as an Anti-TNF Agent

The ability of the compounds of this invention as ex vivo TNFα inhibitors is assessed in the rat. Briefly, groups of male Wistar Alderley Park (AP) rats (180–210 g) are dosed with compound (6 rats) or drug vehicle (10 rats) by the appropriate route e.g. peroral (p.o.), intraperitoneal (i.p.), subcutaneous (s.c.). Ninety minutes later rats are sacrificed using a rising concentration of $CO_2$ and bled out via the posterior vena cavae into 5 Units of sodium heparin/ml blood. Blood samples are immediately placed on ice and centrifuged at 2000 rpm for 10 min at 4° C. and the harvested plasmas frozen at −20° C. for subsequent assay of their effect on TNFα production by LPS-stimulated human blood. The rat plasma samples are thawed and 175 µl of each sample are added to a set format pattern in a 96 U well plate. Fifty µl of heparinized human blood is then added to each well, mixed and the plate is incubated for 30 min at 37° C. (humidified incubator). LPS (25 µl; final concentration 10 µg/ml) is added to the wells and incubation continued for a further 5.5 hours. Control wells are incubated with 25 µl of medium alone. Plates are then centrifuged for 10 min at 2000 rpm and 200 µl of the supernatants are transferred to a 96 well plate and frozen at −20° C. for subsequent analysis of TNF concentration by ELISA.

Data analysis by dedicated software calculates for each compound/dose:

$$\text{Percent inhibition of } TNF\alpha = \frac{\text{Mean } TNF\alpha \text{ (Controls)} - \text{Mean } TNF\alpha \text{ (Treated)} \times 100}{\text{Mean } TNF\alpha \text{ (Controls)}}$$

Test as an Anti-arthritic Agent

Activity of a compound as an anti-arthritic is tested in the collagen-induced arthritis (CIA) as defined by D. E. Trentham et al., (1977) J. Exp. Med. 146,:857. In this model acid soluble native type II collagen causes polyarthritis in rats when administered in Freunds incomplete adjuvant. Similar conditions can be used to induce arthritis in mice and primates.

Test as an Anti-cancer Agent

Activity of a compound as an anti-cancer agent may be assessed essentially as described in I. J. Fidler (1978) Methods in Cancer Research 15:399–439, using for example the B16 cell line (described in B. Hibner et al., Abstract 283 p75 10th NCI-EORTC Symposium, Amsterdam Jun. 16–19, 1998).

Test as an Anti-emphysema Agent

Activity of a compound as an anti-emphysema agent may be assessed essentially as described in Hautamaki et al (1997) Science, 277: 2002.

The invention will now be illustrated but not limited by the following Examples.

In the Examples, low resolution mass spectra and accurate mass determination were recorded on a Hewlett-Packard 1100 LC-MS system equipped with APCI ionisation chamber. NMR spectra were taken on Varian 400 (400 MHz) with TMS as internal standard. All solvents and commercial reagents were laboratory grade and used as received.

Abbreviations used include: AcOH acetic acid; DCC dicyclohexylcarbodiimid; DCM dichloromethane; EtOAc ethyl acetate; TEA triethylamine; DIPEA diisopropyl ethylamine; TBME- ert.butyl methyl ether; THF tetrahydrofuran; Boc tert-butyloxycarbonyl; RT room temperature; TLC thin layer chromatography; LC/MS liquid chromatography/mass spectrometry; DMSO dimethyl sulfoxide; DMSO-D6 deuterated dimethyl sulfoxide; PPh$_3$ triphenylphosphine; DEAD diethyl azodicarboxylate.

Synthesis of Starting Materials

3-Amino Pyrrolidinones and Pyrrolidinediones

Some succinyl-based starting materials were prepared according to the scheme below (modified from Witiak, D. T. et al, 1971, J. Med. Chem. 14(1): 24–30):

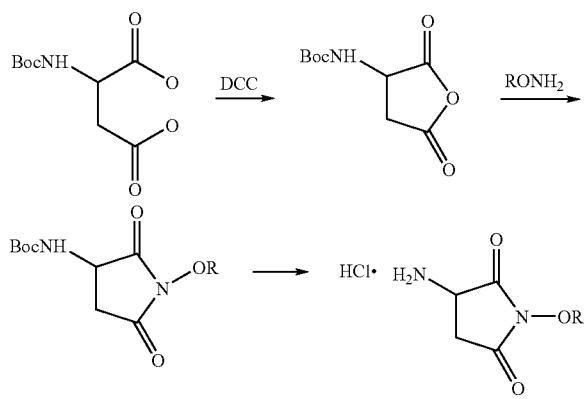

The corresponding N-Boc protected amino acid (0.025 mol) was dissolved in dichloromethane and cooled to –20° C. under chlorcalcium tube.Then, DCC (5.15 g, 0.025 mol) was added at once and the mixture was stirred for 3 hrs and the temperature was allowed to reach RT. Dicyclohexylurea was filtered and washed with two small portions of DCM, and 0.025 g of the O-protected hydroxylamine was added (Benzyl or tert-butyl derivative), followed by 3.4 ml (0.026 mol) of triethylamine.The mixture was stirred for 2 hrs at RT, evaporated to dryness, distributed between ethyl acetate and saturated aquous NaHCO3, the aquous phase was re-extracted with 5 portions of ethyl acetate, pooled organic extracts were washed with water, brine, dried overmagnesium sulfate, evaporated and heated in 30 ml of toluene under reflux for 8 hrs. After the reaction mixture was cooled the compound crystallised. It was filtered and dried in vacuo. The following Boc-derivatives were prepared:

A) t-butyl 1-(tert-butoxy)-2,5-dioxo-3-(R)-pyrrolidinylcarbamate.
1H NMR (Chloroform):1.22 s (9H), 1.28 s (9H), 2.80 m (1.1H) and 3.05 m (1H) (CH2), 4.25 m (1H) (CH—N), 5.5 bs(1.2H), (NH), B) t-butyl 1-(tert-butoxy)-2,5-dioxo-3-(S)-pyrrolidinylcarbamate.
1H NMR (Chloroform):1.22 s (9H), 1.28 s (9H), 2.80 m (1.1H) and 3.05 m (1H) (CH2), 4.25 m (1H) (CH—N), 5.5 bs(1.2H), (NH), C) t-butyl 1-(benzyloxy)-2,5-dioxo-3-(R)-pyrrolidinylcarbamate
1H NMR (Chloroform):1.55 s (9H), 2.75 m(1.1H), 3.1 s (1H), CH$_2$, 4.15 m (0.9H) CH—N, 5.1 s (2H), 7.65 m (5H)

D) t-butyl 1-(benzyloxy)-2,5-dioxo-3-(S)-pyrrolidinylcarbamate
1H NMR (Chloroform):1.55 s (9H), 2.75 m(1.1H), 3.1 s (1H), CH$_2$, 4.15 m (0.9H) CH—N, 5.1 s (2H), 7.65 m (5H)

Each BOC-derivative (2 mmol) was dissolved in 30 ml of 4N HCl in dioxane.The mixture was stirred gently for 30 min. The white precipitate falled. Then, 70 ml of diethyl ether were added, and the mixture was stored at the fridge for 3 hrs. The thick, white precipitate was filtered, washed with ether and dried in vacuo. The following hydrochloride compounds were prepared:

E) R-3-amino-1-(benzyloxy)-2,5-pyrrolidinedione hydrochloride
The BOC-derivative C was used in the above general procedure.
1H NMR: (chloroform) 1.36 s (9H), 3.62 m (1.1H), 3.9 m (0.8H), 4.25 (1.1H)

F) S-3-amino-1-(benzyloxy)-2,5-pyrrolidinedione hydrochloride
The BOC-derivative D was used in the above general procedure.
1H NMR: (chloroform) 1.36 s (9H), 3.62 m (1.1H), 3.9 m (0.8H),4.25 (1.1H)

G) R-3-amino-1-(tert-butoxy)-2,5-pyrrolidinedione hydrochloride
The BOC-derivative A was used in the above general procedure.
1 H NMR (chloroform):2.60 dd (1.2H), 3.2 q(0.9H), 4.4 m (1H), 5.1 s (2H), 7.5 m (5H)

H) S-3-amino-1-(tert-butoxy)-2,5-pyrrolidinedione hydrochloride
The BOC-derivative B was used in the above general procedure.
1 H NMR (chloroform):2.60dd (1.2H), 3.2q(0.9H), 4.4m (1H), 5.1 s (2H), 7.5 m (5H)

I) (3R)-3-Amino-1-benzyloxy-pyrrolidin-2-one trifluoroaceticetate
Was prepared as described in EP0318 091.
Alternative preparation of chiral 3-Amino-1-benzyloxy-pyrrolidin-2-ones:

J) Methyl (2R)-4-[(benzyloxy)amino]-2-[(tert-butoxy-carbonyl)amino]butanoate
J1) To a stirred solution of methyl (2R)-4-[(benzyloxy)imino]-2-[(tert-butoxycarbonyl)-amino]butanoate (1.7 g, 5.0 mmoles) and dry methanol (50 mL) was added sodium cyanoborohydride (0.31 g, 5.0 mmoles) followed dropwise addition of a 1M solution of 4-toluenesulfonic acid (N.B. crystal water present in commercial 4-toluenesulfonic acid has to be removed by azeotropic evaporation with benzene or toluene prior to use) in dry methanol at such a rate so as to keep pH of the mixture at 3–4 (moist indicator paper). After stirring at 22° C. for 2.5 hours TLC and LC indicated a complete reaction. The methanol was stripped off by rotary evaporation leaving a white solid which was taken up in ethyl acetate (100 mL), washed with saturated sodium bicarbonate solution and brine and dried over anhydrous sodium sulfate. Filtration and concentration by rotary evaporation gave 1.7 g of a crude which was chromato-graphed on silica with ethyl acetate/n-heptane (1:5 through 1:3) as eluents. To rid the product from traces of O-benzylhydroxylamine it was chromatographed once more on silica using dichloromethane and dichloromethane/methanol (98:2) as eluents to afford 0.83 g (49% yield) of the subtitle compound as a colourless oil. MS (APCI) m/z 339 (M+1). $^1$H NMR (CDCl$_3$) δ 7.40–7.27 (m, 5H), 5.47 (br d, J=8 Hz, 1H), 4.74 (s, 2H), 4.41–4.31 (m, 1H), 3.72 (s, 3H), 3.10–2.93 (m, 2H), 2.20–2.05 (m, 1H), 1.88–1.78 (m, 1H) and 1.43 (s, 9H) ppm.

J2) Methyl (2R)-4-[(benzyloxy)amino]-2-[(tert-butoxycarbonyl)amino]butanoate (0.74 g, 2.2 mmoles), dry methanol (27 mL) and 0.71 M sodium methoxide in methanol (0.31 mL, 0.22 mmoles) were stirred under dry nitrogen at 22° C. for 3 hours, neutralised with 10% acetic acid and concentrated by rotary evaporation to give a white solid. This was re-dissolved in dichloromethane (10 mL), mixed with silica (2 g), concentrated again and then applied on a silica column. Elution with ethyl acetate/n-heptane (1:4 through 1:1) gave the 0.55 g (82% yield) of the subtitle compound as a white solid.

MS (APCI) m/z 206 (M−99). $^1$H NMR (CDCl$_3$) δ 7.45–7.35 (m's, 5H), 5.03 (d, J=10 Hz, 1H), 5.02 (br s, 1H), 4.97 (d, J=10 Hz, 1H), 4.14–4.02 (m, 1H), 3.25–3.17 (m's, 2H), 2.55–2.40 (m, 1H), 1.77 (ddd, J$_1$=9 Hz, J$_2$=12 Hz, J$_3$=19 Hz; 1H) and 1.44 (s, 9H) ppm. Chiral chromatography [Chiralpak AD (250 mm×4.6 mm) with ethanol-isohexane (65:35) as eluent at 0.45 mL/min flow]: retention time: 11.4 minutes (89% e.e).

(3R)-3-Amino-1-benzyloxy-pyrrolidin-2-one trifluoroacetic acid salt

A solution of tert-butyl-(3R)-1-(benzyloxy)-2-oxopyrrolidinyl-3-carbamate (0.54 g, 1.8 mmoles), trifluoroacetic acid (5 mL) and dichloromethane (15 mL) was stirred at 22° C. for 60 minutes and then concentrated by rotary evaporation to give the title compound as an offwhite solid. MS (APCI) m/z 207 (M+1). $^1$H NMR (CD$_3$OD) δ 7.50–7.37 (m's, 5H), 5.02 (d, J=11 Hz, 1H), 4.99 (d, J=11 Hz, 1H), 4.03 (t, J=9 Hz, 1H), 3.56–3.46 (m, 2H), 2.56–2.47 (m, 1H), and 2.03–1.92 (m, 1H) ppm.

K) (3S)-3-Amino-1-benzyloxy-pyrrolidin-2-one trifluoroacetic acid salt

Methyl (2S)-4-[(benzyloxy)imino]-2-[(tert-butoxycarbonyl)amino]butanoate was prepared as described for methyl (2R)-4-[(benzyloxy)imino]-2-[(tert-butoxycarbonyl)-amino]butanoate in J1) by changing the starting material from D- to L-homoserine. This material is then subjected to the operations described in J2) above. tert-Butyl-(3S)-1-(benzyloxy)-2-oxopyrrolidinyl-3-carbamate Chiral chromatography [Chiralpak AD (250 mm×4.6 mm) with ethanol-isohexane (65:35) as eluent at 0.45 mL/min flow]: retention time: 12.9 minutes (88% e.e). Treatment of this material as described in Example J) gave the title compound as a white solid MS (APCI) m/z 207 (M+1). $^1$H NMR (CD$_3$OD) δ 7.50–7.37 (m's, 5H), 5.02 (d, J=11 Hz, 1H), 4.99 (d, J=11 Hz, 1H), 4.03 (t, J=9 Hz, 1H), 3.56–3.46 (m, 2H), 2.56–2.47 (m, 1H), and 2.03–1.92 (m, 1H) ppm.

L) (3R,5S)-3-Amino-1-(benzyloxy)-5-isopropyl-2-pyrrolidinone trifluoroacetate;

M) (3R,5S)-3-Amino-1-(benzyloxy)-5-isopropyl-2-pyrrolidinone trifluoroacetate

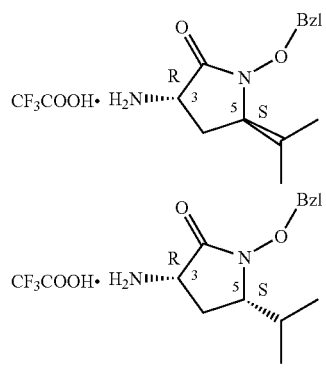

N) Methyl (2R)-2-[(tert-butoxycarbonyl)amino]-4-hydroxybutanoate

D-Homoserine (5.0 g, 42 mmoles) was suspended in a solution of dry methanol (74 mL) and N-ethyldiisopropylamine (15 mL, 88 mmoles). To the stirred mixture was added in a dropwise manner a solution of di-tert-butyl dicarbonate (9.2 g, 42 mmoles) and dioxane (37 mL) at 22° C. After the addition was completed in 20 minutes the clear solution was stirred at the same temperature for 3.5 hours, then concentrated by rotary evaporation. The oily residue was dissolved in toluene (150 mL) and concentrated by rotary evaporation. This operation was repeated once to give the N-protected amino acid as a vicous oil. This was dissolved in dry N,N-dimethylformamide (110 mL) under dry nitrogen. Finely ground potassium hydrogencarbonate (5.0 g, 50 mmoles) and iodomethane (2.9 mL, 47 mmoles) were added and the mixture was stirred at 22° C. for 70 hours. The suspension was suction filtered and the clear filtrate was concentrated by rotary evaporation using a warm water bath (38° C.). The remaining oil was taken up in ethyl acetate (300 mL) and washed with a solution of water (50 mL) and 10% sodium thiosulfate (5 mL). The aqueous phase was separated and washed with ethyl acetate (4×200 mL). The combined organic phases were washed with brine (300 mL) saturated with potassium hydrogencarbonate, dried with anhydrous sodium sulfate, suction filtered and concentrated by rotary evaporation using a high vacuum pump to afford approx. 9.7 g (95% yield) of the sub-title compound as a thick, yellow oil. $^1$H NMR (CDCl$_3$) δ 5.36 (d, 1H), 4.50 (m, 1H), 3.77 (s, 3H),3.76–3.60 (m, 2H), 2.15 (m, 1H), 1.62 (m, 1H) and 1.45 (s, 9H) ppm.

O) Methyl (2R)-2-[(tert-butoxycarbonyl)amino]-4-oxobutanoate

A solution of oxalyl chloride (4.0 mL, 46 mmoles) and dry dichloromethane (150 mL) under dry nitrogen was cooled to −78° C. on a dry-ice/acetone bath. To it was added dimethylsulfoxide (6.5 mL, 92 mmoles) in a dropwise manner while keeping the internal temperature below −65° C. (exothermic reaction!). When the addition was completed a solution of crude methyl (2R)-2-[(tert-butoxycarbonyl)- amino]-4-hydroxybutanoate (42 mmoles) and dry dichloromethane (300 mL) was added during two hours while keeping the internal temperature below −70° C. The stirring was continued for another 30 minutes at −78° C., then triethylamine (29 mL, 208 mmoles) was added quickly. After 5 minutes the cooling bath was withdrawn and the solution was warmed to 22° C. After a total reaction time of eight hours the dark orange solution was diluted with dichloromethane (200 mL), washed with brine (350 mL), dried with anhydrous sodium sulfate, filtered and concentrated by rotary evaporation to afford 13.5 g of a dark orange oil. The oil was taken up in dichloromethane (50 mL), mixed with silica (20 g) and then concentrated on a water bath (35° C.) by rotary evaporation. The product thus obtained was applied on a silica column (5 cm diam) and elution with ethylacetate/n-heptane (1:3 through 1:1) afforded 3.7 g (38% overall yield from three steps) of the title compound as a colourless oil. FT-IR (film) v 1715 cm$^{-1}$ (v str). $^1$H NMR (CDCl$_3$) δ 9.72 (s, 1H), 5.38 (d, 1H), 4.58 (m, 1H), 3.73 (s, 3H), 3.08 (dd, 1H), 2.99 (dd, 1H) and 1.42 (s, 9H) ppm.

P) Methyl (2R)-4-[(benzyloxy)imino]-2-[-(tert-butoxycarbonyl)amino]butanoate

Methyl (2R)-2-[(tert-butoxycarbonyl)amino]-4-oxobutanoate (3.7 g, 16 mmoles), dry pyridine (35 mL), O-benzylhydroxylamine (2.0 g, 16 mmoles) and anhydrous sodium sulfate (4 g) were stirred under dry nitrogen at 22° C. for 90 minutes. The solution was filtered by suction and concentrated twice with toluene (50 mL) by rotary evaporation to afford an oil (5.3 g) which was purified on a silica column eluted with ethylacetate/n-heptane (1:5 through 1:3). Concentration of pure fractions gave 4.1 g (76% yield) of the title compound as a colourless oil. $^1$H NMR (CDCl$_3$) δ 7.39 (t, 0.66 H), 7.36–7.26 (m, 5H), 6.76 (t, 0.33H), 5.19 (m, 1H), 5.10 (s, 0.8H), 5.02 (s, 1.2H), 4.48 (m, 1H), 3.71 (s, 1.2H), 3.66 (s, 1.8H), 2.91–2.71 (m, 1H), 2.67 (m, 1H), 1.43 (s, 5H) and 1.43 (s, 4H) ppm.

Q) tert-Butyl-(3R)-1-(benzyloxy)-5-isopropyl-2-oxopyrrolidinyl-3-carbamate

To a solution of methyl (2R)-4-[(benzyloxy)imino]-2-[(tert-butoxycarbonyl)amino]-butanoate (2.8 g, 8.3 mmoles), 2-iodopropane (8.3 mL, 83.5 mmoles) and dry toluene (160 mL) under dry nitrogen were added borontrifluoride etherate (3.2 mL, 25 mmoles) and 1M triethylborane in hexane (21 mL, 21 mmoles). Atmospheric air (40 mL) was rapidly flushed through the solution using a syringe. After stirring the mixture for 20 minutes at 22° C. it was poured into saturated sodium hydrogencarbonate solution (250 mL). The two phases were partitioned, the aqueous phase was washed once with toluene (100 mL) and the combined organic phases were washed with brine, dried with anhydrous sodium sulfate, filtered and concentrated by rotary evaporation to give 2.8 g of an oil. Column chromatography on silica using ethylacetate/n-heptane (1:8 through 1:2) as eluent gave 0.81 g of unreacted starting material and 0.67 g (21% yield) of Methyl (2R)-4-[(benzyloxy)amino]-2-[(tert-butoxycarbonyl)amino]-5-methylhexanoate as a diastereomeric mixture. $^1$H NMR (CDCl$_3$) δ 7.41–7.26 (m, 5H), 5.93 (br d, 0.4H), 5.61 (br d, 0.6H), 4.86–4.64 (br m, 2H), 4.42 (br m, 0.51), 4.25 (br m, 0.5H), 3.72 (s, 1.4H), 3.67 (s, 1.6H), 2.90–2.76 (br m, 0.6H), 2.76–2.61 (br m, 0.4H), 2.18–1.54 (m's, 3H), 1.44 (s, 9H), 0.90 (d, 3H) and 0.86 (d, 3H) ppm. MS (APCI) m/z 381 (M+1).

R) tert-butyl-(3R,5S)-1-(benzyloxy)-5-isopropyl-2-oxopyrrolidinyl-3-carbamate;

S) tert-butyl-(3R,5R)-1-(benzyloxy)-5-isopropyl-2-oxopyrrolidinyl-3-carbamate 0.33 g of Methyl (2R)4-[(benzyloxy)amino]-2-[(tert-butoxycarbonyl)amino]-5-methylhexanoate was purified by preparative chromatography [Kromasil™ (250 mm×50.8 mm) from 45 through 65% acetonitrile to water (0.1% TFA) during 60 minutes at 40 mL/min flow]. Diastereomerically pure fractions as seen from analytical HPLC were pooled and concentrated to dryness by rotary evaporation on a warm water bath. Analysis by $^1$H NMR and LC-MS showed that the isolated products corresponded to the pyrrolidinones and not to the hydroxylamines! Spontaneous ring closure occurred either during the separation step or upon concentration of the fractions.

Early fractions (retention time 46–48 min): 0.13 g colourless oil

Corresponds to tert-butyl-(3R,5S)-1-(benzyloxy)-5-isopropyl-2-oxopyrrolidinyl-3-carbamate i.e. the trans-isomer.

LC-MS (APCI) m/z 293 (M-55), 249 (M-99). $^1$H NMR (CDCl$_3$) δ5–7.35 (m, 5H), 5.07 (d, 1H), 5.01 (q, 2H), 4.15 (m, 1H), 3.40 (d, 1H), 2.35 (m, 1H), 2.09 (m, 1H), 1.80 (m, 1H), 1.45 (s, 9H), 0.90 (d, 3H) and 0.80 (d, 3H) ppm. $^{13}$C NMR (CDCl$_3$) δ 167.5, 155.6, 134.6, 129.3, 128.8, 128.4, 80.1, 76.5, 61.0, 48.9, 28.9, 28.3, 27.4, 18.3 and 16.1 ppm.

Late fractions (retention time 51–52 min): 0.087 g colourless oil

Corresponds to tert-butyl-(3R,5R)-1-(benzyloxy)-5-isopropyl-2-oxopyrrolidinyl-3-carbamate i.e. the cis-isomer.

LC-MS (APCI) m/z 293 (M-55), 249 (M-99). $^1$H NMR (CDCl$_3$) δ 7.44–7.34 (m, 5H), 5.07 (d, 1H), 4.92 (d, 1H), 4.12 (m, 1H), 3.24 (m, 1H), 2.40 (m, 1H), 2.13 (m, 1H) 1.44 (s, 9H), 0.83 (d, 3H) and 0.81 (d, 3H) ppm. $^{13}$C NMR (CDCl$_3$) δ 167.9, 155.7, 134.5, 129.6, 129.0, 128.5, 80.2, 76.2, 60.3, 49.2, 28.3, 27.5, 27.2, 17.9 and 15.4 ppm.

T) (3R,5S)-3-Amino-1-(benzyloxy)-5-isopropyl-2-pyrrolidinone trifluoroacetate

A solution of tert-butyl-(3R,5S)-1-(benzyloxy)-5-isopropyl-2-oxopyrrolidinyl-3-carbamate (0.13 g, 0.37 mmoles), trifluoroacetic acid (1 mL) and dichloromethane (3 mL) was stirred under nitrogen at 22° C. for 20 minutes and then concentrated by rotary evaporation to give 0.14 g of the title compound as a white solid. LC-MS (APCI) m/z 249 (M+1). $^1$H NMR (CDCl$_3$) δ 7.40–7.30 (m, 5H), 4.97 (d, 1H), 4.91 (d, 1H), 4.12 (m, 1H), 3.62 (m, 1H), 2.20 (m, 1H), 2.10 (m, 1H), 0.81 (d, 3H) and 0.74 (d, 3H) ppm.

U) (3R,5R)-3-Amino-1-(Benzyloxy)-5-isopropyl-2-pyrrolidinone trifluoroacetate

A solution of tert-butyl-(3R,5R)-1-(benzyloxy)-5-isopropyl-2-oxopyrrolidinyl-3-carbamate (0.035 g, 0.10 mmoles), trifluoroacetic acid (0.34 mL) and dichloromethane (1 mL) was stirred under nitrogen at 22° C. for 30 minutes and then concentrated by rotary evaporation to give 0.041 g of the title compound as a colourless oil. LC-MS (APCI) m/z 249 (M+1). $^1$H NMR (CDCl$_3$) δ 7.33 (app s, 5H), 4.96 (d, 1H), 4.85 (d, 1H), 4.10 (mn, 1H), 3.32 (m, 1H), 2.06 (m, 1H), 1.84 (m, 1H) and 0.78 (d, 6H) ppm.

Sulfonyl and Sulfamoyl Chlorides

V) 3-Benzylsulfanylmethyl-dihydro-furan-2-one. [91496-15-0]

3-Methylene-dihydro-furan-2-one (4.6 g; 46.9 mmol), Benzylmercaptan (4.3 ml; 36.5 mmol) was dissolved in MeOH (30 ml) and 30% TritonB (=Benzyltrimethylammonium hydroxide) (2 ml; approx 3.6 mmol) was added. The mixture was stirred at room temperature over night. Evaporation of solvent and residue was distributed between 5% HCl (50 ml) EtOAc (10 ml). The water phase was extracted twice with EtOAc. The combined organic phases was washed with saturated NaHCO$_3$ (aq), dried (MgSO$_4$), filtered and evaporated. The resulting oil was distilled, to give the title compound as a colourless oil. Obtained 3.6 g (44% yield).

B.p=120–122° C. at 0.05 torr GC-MS: M$^+$=222.3, purity>98%. $^1$H-NMR(CDCl$_3$): δ 7.31–7.16 (m, 5H, Ar—H), 4.23+4.06 (dt+dt, 1H+1H, —CH$_2$OCO—), 3.69 (s, 2H, ArCH$_2$S—), 2.86+2.52 (dd+dd, 1H+1H, —SCH$_2$CH—), 2.66 (ddd, 1H, —CH(CO—)CH$_2$—), 2.29+1.98 (m+m, 1H+1H, —CHH$_2$CH$_2$O—) ppm. $^{13}$C-NMR(CDCl$_3$): δ 177.39, 137.62, 128.51, 128.19, 126.80, 66.25, 39.29, 36.57, 31.33, 27.60 ppm.

W) Clorosulfonylmethyl-dihydro-furan-2-one (3R,S)-3-Benzylsulfanylmethyl-dihydro-furan-2-one (1.25 g; 5.65 mmol) was dissolved in Dioxane (30 ml)+H$_2$O (20 ml) and cooled on a ice-water bath. While stirring Cl$_2$ (g) was slowly bubbled through the cold solution until the solution became green-yellow in colour, the chlorine gas was then turned off and the solution stirred for 15 min on the ice-bath. The solvent was then removed by evaporation and the residue was redissolved and evaporated from Toluene four times. The intermediate sulfonyl chloride obtained as an oil was not isolated.

X) 4-(4Fluoro-phenyl)-piperidine-1-sulfonyl chloride 4-(4Fluoro-phenyl)-piperidine hydrochloride (1.0 g; 4.64 mmol) and Et$_3$N (1.9 ml; 13.9 mmol) was dissolved in DCM (20 ml) and cooled to 0° C. using an ice/water bath. ClSO$_3$H (309 ul; 4.6 mmol) was slowly added droppwise due to highly exothermic reaction. After addition was compleat the mixture was allowed to reach room temperature and stirred over night. The clear yellow solution of the intermediate sulfonicacid derivative was evaporated and dry Toluene (20 ml) was added to form a slurry. To this slurry was added PCl$_5$ (1.06 g; 5.1 mmol) in portions, the mixture was heated on an oil bath to 75° C. for 2 h, and then left over night in room temperature before filtration. The filtercake was washed with Toluene and the filtrate was evaporated. EtOAc was added and precipitating salts was removed by filtration. The crude product was purified on 70 g Si-60 gel using flash chromatography with a gradient 100% Heptane to 100% DCM. Gradient time was 35 min and flow of solvent was 20 ml/min. Fractions containing product was evaporated to give the title compound as a slightly yellow oil that crystallises upon standing. Obtained 0.94 (70% yield) of the title compound.

TLC(Si-60, DCM:Heptan (8:2)): R$_f$=0.76 Purity by NMR=95% $^1$H-NMR(CDCl$_3$): δ 7.19+7.04 (m+m, 2H+2H, Ar—H), 4.03+2.94(m+m, 2H+2H, —N(CH$_2$—)$_2$—), 2.69 (m, 1H, ArCH—), 2.08–1.86 (m, 4H, —N(CH$_2$CH$_2$—)$_2$—)$_2$—) ppm. $^{13}$C-NMR(CDCl$_3$): δ 162.86, 160.43, 139.56, 139.53, 128.08, 128.00, 115.63, 115.42, 48.57, 40.44, 31.76 ppm.

Y) 3-(4-Fluoro-phenoxy)-pyrrolidine-1-sulfonyl chloride (3R,S)-3-(4-Fluoro-phenoxy)-pyrrolidine (Helsley, G. C., 1970, German patent number 1964511; Welstead, W. J., Jr. et al, 1969, J. Med. Chem. 12(3): 435–41), (1.0 g; 5.5 mmol), and Et$_3$N (1.5 ml; 11.0 mmol) was dissolved in DCM (20 ml) and cooled to 0° C. using ice/water bath. ClSO$_3$H (367 ul; 5.5 mmol) was added slowly droppwise due to highly exothermic reaction. After addition was compleat the mixture was allowed to reach room temperature and stirred over night. The clear yellow solution of the intermediate sulfonicacid derivative was evaporated and dry Toluene (20 ml) is added to form a slurry. To this slurry was added PCl$_5$ (1.26 g; 6.05 mmol) in portions, the mixture was heated on an oilbath to 75° C. for 2 h, and then left over night in room temperature before filtration. The filtercake was washed with Toluene and the filtrate was evaporated. EtOAc was added and precipitating salts was removed by filtration. The crude product was purified on 70 g Si-60 gel using flash chromatography with a gradient 100% Heptane to 100% DCM. Gradient time was 35 min and flow of solvent was 20 ml/min.

Fractions containing product was evaporated to give the title compound as a colourless oil that crystallises upon standing. Obtained 1.17 g (76% yield).

TLC (Si-60 DCM:Heptane (8:2)): R$_f$=0.74 $^1$H-NMR (CDCl$_3$): δ 7.02+6.84 (m+m, 2H+2H, Ar—H), 4.96 (m, 1H, ArOCH—), 3.78–3.76 (m, 4H, —NCH$_2$(CH$_2$—)—), 2.36+2.25 (m+m, 1H+1H, —NCH$_2$CH$_2$—) ppm. $^{13}$C-NMR (CDCl$_3$): δ 159.04, 156.65, 152.23, 152.24, 116.97, 116.89, 116.39, 116.16, 76.05, 55.20, 48.64, 31.18 ppm.

Z) 4-(4-Trifluoromethyl-phenyl)-piperazine1-sulfonyl chloride 1-(4-Trifluoromethyl-phenyl)-piperazine (1.0 g; 4.34 mmol) and Et$_3$N (1.21 ml; 8.68 mmol) was dissolved in DCM (20 ml) and cooled to 0° C. on an ice/water bath. ClSO$_3$OH (289 ul; 4.34 mmol) was added dropwise, after addition the mixture was allowed to reach room temperature and stirred over night. The resulting yellow clear solution was evaporated and the residue was evaporated once from Toluene. To the intermediate sulfonic acid was added Toluene (20 ml) to form a slurry, to this slurry was added PCl$_5$ (1.0 g; 4.8 mmol) in portions, the mixture was then heated on an oil-bath to 75° C. for 2 h. and then stirred at room temperature over night.

The reaction mixture was filtered and the filter cake was washed with Toluene and the combined organic solvents evaporated. The residue was dissolved in EtOAc and the insoluble salts removed by filtration. Si-60 gel was added to the clear solution and then evaporated to give the crude product absorbed onto silica-gel. Purified by flash chromatography on 70g of Si-60 gel using a gradient solvent system 100% Heptane to 100% DCM, gradient time 44 min, eluent flow: 20 ml/min.

Fractions containing the product was evaporated to the title compound as a slightly yellow solid. Obtained 0.65 g (45% yield)

Purity by NMR=98% TLC(Si-60, DCM:Heptane (8:2)): R$_f$=0.82 $^1$H-NMR(CDCl$_3$): δ 7.55+6.98 (d+d, 2H+2H, Ar—H), 3.50 (brs, 8H, —CH$_2$-×4) ppm. $^{13}$C-NMR(CDCl$_3$): δ 152.19, (162.75+126.71+126.67+126.63), (128.42+125.73+123.03+120.34), (122.95+122.62+122.30+121.97), 115.78, 47.42, 47.30 ppm.

EXAMPLE 1

3-[4-(4-Fluoro-phenyl)-piperazine-1-sulfonylmethyl]-1-hydroxy-pyrrolidin-2-one

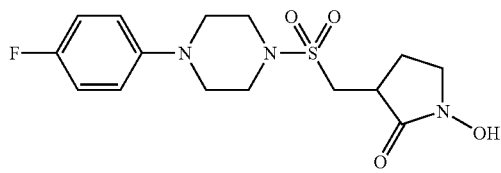

a) 3-[4-(4-Fluoro-phenyl)-piperazine-1-sulfonylmethyl]-dihydro-furan-2-one

Clorosulfonylmethyl-dihydro-furan-2-one was dissolved in DCM (10 ml) and added to a cold (0° C.) solution of 4-fluoro-phenyl piperazine (1.15 g; 6.38 mmol) and Et$_3$N (0.87 ml; 6.2 mmol) in DCM (7 ml). The reaction mixture was stirred at room temperature for 2 h. Evaporation of solvent and purification by flash chromatography on Si-60 gel using EtOAC:Heptane (1:1) as eluent. The fractions containing the product was evaporated to give the title compound. Obtained 0.94 g (48% yield). Purity estimated by NMR to be 90%, considered pure enough to use in next step.

TLC (Si-60, EtOAc:Heptane (1:1)): R$_f$=0.26 LC/MS (APCI): MH$^+$=343.0 $^1$H-NMR(CDCl$_3$): δ 6.99+6.90 (m+m, 2H+2H, Ar—H), 4.47+4.28 (m+m, 1H+1H, —CH$_2$OCO—), 3.57+2.92 (dd+dd, 1H+1H, —SO$_2$CH$_2$—), 3.46+3.19 (m+m, 4H+4H, —N(CH$_2$—)—×4), 3.14 (m, 1H, —CH(CO—)CH$_2$—), 2.77+2.26 (m+m, 1H+1H, —CH$_2$CH$_2$O—) ppm. $^{13}$C-NMR(CDCl$_3$): δ 176.42, 159.04, 156.65, 147.31, 147.28, 119.07, 118.99, 115.88, 115.66, 67.09, 50.53, 49.21, 45.73, 35.41, 29.14 ppm.

b) N-tert-Butoxy-2-[4-(4-fluoro-phenyl)-piperazine-1-sulfonylmethyl]-4-hydroxy-butyramide O-t-Butyl-Hydroxylamine hydrochloride (283 mg; 2.25 mmol) was suspended in dry benzene (10 ml). (Toluene can be used instead of benzene). Trimethylaluminium (2.0M/heptane) (1.20 ml; 2.4 mmol) was added to the slurry under nitrogen. Methane gas evolved and an almost clear solution was formed. (3R,S)-3-[4-(4-Fluoro-phenyl)-piperazine-1-sulfonylmethyl]-dihydro-furan-2-one (350 mg; 1.03 mmol) was dissolved in benzene (10 ml) and added to the aluminate reagent during 5 min. The mixture was stirred at room temperature for 60 min. The reaction was quenched by EtOH (5 ml) and stirred over night, diluted with 1M AcOH (aq) (10 ml) and extracted with 4 portions of EtOAc. The organic phases was evaporated and the crude product was purified on silica using DCM as first eluent followed by DCM/MeOH (100/4) as second eluent. The fractions containing the product was evaporated to give the title compound.

Obtained 0.39 g (88.5% yield) TLC(Si-60, DCM:MeOH (100:3)): R$_f$=0.1 LC/MS(APCI): MH$^+$=431.9 $^1$H-NMR (DMSO-D6): δ 10.48 (s, 1H, —NH—), 7.07+6.98 (m+m, 2H+2H, Ar—H), 4.55 (brt, 1H, —OH), 3.47–3.34 (m, 3H), 3.30–3.23 (m, 4H), 3.17–3.10 (m, 5H), 2.77 (m, 1H), 1.66 (q, 2H), 1.15 (s, 9H) ppm.

c) 1-tert-Butoxy-3-[4-(4-fluoro-phenyl)-piperazine-1-sulfonylmethyl]-pyrrolidin-2-one (2R,S)-N-tert-Butoxy-2-[4-(4-fluoro-phenyl)-piperazine-1-sulfonylmethyl]-4-hydroxy-butyramide (100 mg; 0.23 mmol)+PPh$_3$ (90 mg; 0.34 mmol) was dissolved in DCM (5 ml) and cooled under nitrogen to −78° C. DEAD was added and the mixture was allowed to assume room temperature during 3 h. LC/MS showed that starting mtrl was still present in the reaction mixture and that all PPh$_3$ was consumed. Another portion of PPh$_3$ (20 mg; 76 µmol) and DEAD (12 µl; 76 µmol) was added and the reaction mixture was left over night at room temperature. Evaporation of solvent and residue purified on 8 g Si-60 gel using EtOAc: Heptane (3:5) as eluent. Fractions containing the product was evaporated to give the title compound as a colourless solid. Obtained 45 mg (47% yield)

TLC(Si-60, EtOAc:Heptane (1:1)): R$_f$=0.25 LC/MS (APCI):MH$^+$=414.1 $^1$H-NMR(CDCl$_3$): δ 6.99+6.89 (m+m, 2H+2H), 3.60–3.48 (m, 3H), 3.48–3.42 (m, 4H), 3.21–3.15 (m, 4H), 2.99–2.83 (m, 2H), 2.52 (m, 1H), 2.08 (m, 1H), 1.32 (s, 9H) ppm.

d) 3-[4-(4-Fluoro-phenyl)-piperazine-1-sulfonylmethyl]-1-hydroxy-pyrrolidin-2-one (3R,S)-1-tert-Butoxy-3-[4-(4-fluoro-phenyl)-piperazine-1-sulfonylmethyl]-pyrrolidin-2-one (13 mg; 0.03 mmol) was dissolved in neat TFA (1 ml) and heated in a microwave oven at 150 W for 9×10s, allowing the sample to cool between each run in the microwave (reaction followed by LC/MS). Upon evaporation of the solvent, the residue was redissolved in DCM and product trapped onto a short Si-60 gel column. Impurities were washed away using EtOAc: Heptane (3:5), the product was eluted with DCM:MeOH: Et$_3$N (90:10:1) and solvent evaporated. This yellow crude product was dissolved in DCM and filtered through another Si-60 column using EtOAc as solvent, after evaporation the title compound was obtained as a colourless solid. Obtained 5 mg (50% yield, 90% pure by H-nmr)

LC/MS(APCI):MH$^+$=358.0 $^1$H-NMR(DMSO-D6): δ 9.75 (s, 1H, —NOH), 7.07+6.99 (m+m, 2H+2H, Ar—H), 3.44 (m, 2H, —CH$_2$N(OH)—), 3.32+3.16(m+m, 4H+4H, —N(CH$_2$—)—×4 ), 3.31+3.23 (m+m, 1H+1H, —SO$_2$CH$_2$—), 2.82 (m, 1H, —CH(CO—)—), 2.29+1.93 (m+m, 1H+1H, —CH$_2$CH$_2$N(OH)—) ppm.

EXAMPLE 2

3-[4-(4-Fluoro-phenyl)-piperazine-1-sulfonylmethyl]-1-hydroxy-pyrrolidin-2-one Trifluoroacetate.

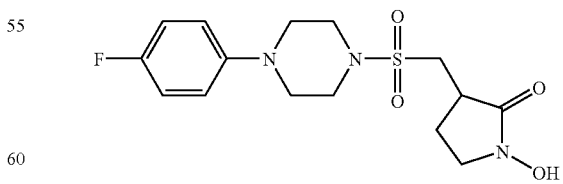

The title compound was prepared according to the method described in Example 1, starting from (3R,S)-1-tert-Butoxy-3-[4-(4-fluoro-phenyl)-piperazine-1-sulfonylmethyl]-pyrrolidin-2-one (45 mg; 0.11 mmol). Purification was made on C-18 column, using MeCN/H$_2$O+0.1 % TFA solvent system, purified twice to give the title compound as a colourless solid. Obtained 40 mg (77% yield).

LC/MS(APCI):MH$^+$=358.1 $^1$H-NMR(DMSO-D6): δ 7.07+6.99 (m+m, 2H+2H, Ar—H), 5.12 (vvbrs, 2H, —OH+NH$^+$), 3.43 (m, 2H, —CH$_2$N(OH)—), 3.32+3.16(m+m, 4H+4H, —N(CH$_2$—)—×4), 3.31+3.23 (m+m, 1H+1H, —SO$_2$CH$_2$—), 2.81 (m, 1H, —CH(CO—)—), 2.29+1.93 (m+m, 1H+1H, —CH$_2$CH$_2$N(OH)—) ppm. $^{13}$C-NMR (DMSO-D6): δ 167.78, 157.59, 155.24, 147.40, 147.38, 118.04, 117.96, 115.48, 115.26, 49.38, 49.15, 46.93, 45.06, 34.68, 22.66 ppm.

EXAMPLE 3

4-(4-Fluoro-phenyl)-piperidine-1-sulfonic acid (1-hydroxy-2-oxo-pyrrolidin-3yl)-amide

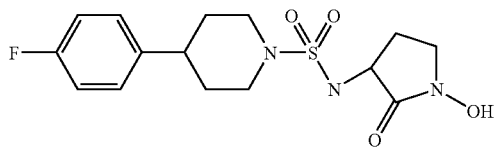

a) 4-(4'-Fluoro-phenyl)-piperidine-1-sulfonic acid (1-benzyloxy-'-oxo-pyrrolidin-3-yl)-amide 3-Amino-1-benzyloxy-pyrrolidin-2-one hydrochloride (68 mg; 0.28 mmol) and DMAP (20 mg; 0.16 mmol) was dissolved in dry DMF (1.5 ml). 4-(4Fluoro-phenyl)-piperidine-1-sulfonyl chloride (155 mg; 0.56 mmol) was dissolved in DMF (0.25 ml) and added to the reaction mixture followed by Et$_3$N (156 ul; 1.12 mmol).

The reaction mixture was heated using a microwave oven at 200 W for 10 seconds. Another portion of the sulfamoyl-chloride (155 mg; 0.56 mmol) in DMF (0.25 ml) and Et$_3$N (156 ul; 1.12 mmol) was added and the mixture was then heated again at 200 W for 10 seconds. The reaction mixture was evaporated, the residue was dissolved in DCM and dry Si-60 gel was added before evaporation to give the crude product absorbed onto silica. Purification was made on 20 g of Si-60 gel, using gradient 100% Heptane to 100% EtOAc, gradient time=44 min, 20 ml/min. Fractions containing the product was evaporated to give the title compound as a colourless solid. Obtained 40 mg (32% yield). Purity was only 85% but considered pure enough to use in the next step.

LC/MS(APCI): MH$^+$=448.1 $^1$H-NMR(CDCl$_3$): δ 7.42 (m, 5H, Ar—H), 7.17 (m+m, 2H+2H, Ar—H), 5.02 (dd, 2H, ArCH$_2$ON—), 4.84 (d, 1H, —NH—), 4.00 (m, 1H, —NHCH—), 3.87+2.98 (m+m, 2H+2H, —N(CH$_2$CH$_2$—)$_2$—), 3.25 (m, 2H, —CH$_2$N(OBzl)—), 2.64 (m, 1H, ArCH(CH$_2$—)$_2$—), 2.51+1.91 (m+m, 1H+1H, —CH$_2$CH$_2$N(OBzl)—), 1.91+1.77 (m+m, 2H+2H, —N(CH$_2$CH$_2$—)$_2$—) ppm.

b) 4-(4-Fluoro-phenyl)-piperidine-1-sulfonic acid (1-hydroxy-2-oxo-pyrrolidin-3yl)-amide 4-(4-Fluoro-phenyl)-piperidine-1-sulfonic acid ((3R,S)-1-benzyloxy-2-oxo-pyrrolidin-3-yl)-amide (40 mg; 0,089 mmol) was dissolved in MeOH (10 ml). A slurry of 5% Pd/BaSO$_4$ (20 mg in 1 ml MeOH) was added under a stream of nitrogen. The mixture was stirred at room temperature and hydrogenated with H$_2$ (g) at 1 atm pressure for 1 h 45 min. The mixture was filtered through celite and the filter-cake was washed with MeOH and EtOAc. The slightly yellow filtrate was evaporated, redissolved in EtOAc and evaporated onto Si-60 gel. The silica bound crude product was purified using 10 g of Si-60 gel, a gradient 100% Heptane to 100% (EtOAc+5% AcOH) during 30 min, and a flow of 20 ml/min. Fractions containing the product was evaporated to give the title compound as a colourless solid.

Obtained 20 mg (62% yield) LC/MS (APCI): MH$^{30}$ =358.1 Purity by NMR >95%. $^1$H-NMR(DMSO-D6): δ 9.82 (brs, 1H, —OH), 7.72 (brs, 1H, —NH), 7.33–7.26+7.15–7.08 (m+m, 2H+2H, Ar—H), 3.93 (brt, 1H, —CH), 3.70 (brm, 1H, —CH'H"NSO$_2$—), 3.60 (brm, 1H, —CH'H"NSO$_2$—), 3.38 (dd, 2H, —CH$_2$N(OH)CO—), 2.85 (m, 2H, —CH'H"NSO$_2$—), 2.62 (m, 1H, Ar—CH—), 2.35+1.79 (m+m, 1H+1H, —CHCH$_2$—), 1.81+1.64 (m+m, 2H+2H, Ar—CHCH$_2$—) ppm $^{13}$C-NMR(DMSO-D6): δ 166.13, 161.95, 159.55, 141.71, 141.68, 128.35, 128.54, 115.12, 114.92, 51.80, 46.12, 45.85, 45.44, 40.23, 32.34, 32.23, 25.58 ppm.

EXAMPLE 4

3-(4-Fluoro-phenoxy)-pyrrolidine-1-sulfonic acid (-1-hydroxy-2-oxo-pyrrolidin-3-yl)-amide

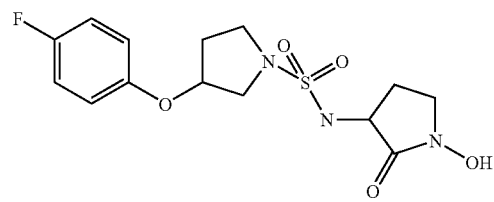

a) 3-(4-Fluoro-phenoxy)-pyrrolidine-1-sulfonic acid (1-benzyloxy-2-oxo-pyrrolidin-3-yl)-amide (3R,S)-3-Amino-1-benzyloxy-pyrrolidin-2-one hydrochloric acid (68 mg; 0.28 mmol) and DMAP (17 mg; 0.14 mmol) was dissolved in dry DMF (1.5 ml). (3R,S)-3-(4-Fluoro-phenoxy)-pyrrolidine-1-sulfonyl chloride (134 mg; 0.48 mmol) was dissolved in DMF (0.25 ml) and added to the reaction mixture followed by Et$_3$N (145 ul; 1.04 mmol). The reaction mixture was heated using a microwave oven at 200 W for 10 seconds. Another portion of the sulfamoyl chloride (134 mg; 0.48 mmol) in DMF (0.25 ml) and Et$_3$N (145 ul; 1.04 mmol) was added and the mixture was heated again at 200 W for 10 seconds. The reaction mixture was evaporated, the residue was dissolved in DCM and dry Si-60 gel was added before evaporation to give the crude product absorbed onto silica. Purification was made on 20 g Si-60, using gradient 100% Heptane to 100% EtOAc, gradient time=44 min, 20 ml/min. Fractions containing the product was evaporated to give the title compound as a colourless solid. Obtained 60 mg (47% yield). Purity was only 85% but considered pure enough to use in the next step.

LC/MS(APCI): MH$^{30}$ =450.1 Purity by HPLC (220 nm)=85% $^1$H-NMR(CDCl$_3$): δ 7.40 (m, 5H, Ar—H), 6.98+6.81 (m+m. 2H+2H, Ar—H), 5.00 (dd, 2H, ArOCH$_2$N—), 4.89 (brm, ArOCH(CH$_2$—)CH$_2$—), 4.31 (m, 1H, —COCH(CH$_2$—)NH—), 3.67 (m, 1H, —N(CH'H"—)CH$_2$CH$_2$—), 3.56 (m, 4H, —N(CH'H"—)CH$_2$CH$_2$—, +NH), 3.22 (m, 2H, —CH₂N(OBzl)—), 2.46+1.90 (m+m, 1H+1H, —CH₂CH₂N(OBzl)—), 2.23 (m, 2H, —N(CH'H")CH₂CH₂—) ppm.

b) 3-(4-Fluoro-phenoxy)-pyrrolidine-1-sulfonic acid (1-hydroxy-2-oxo-pyrrolidin-3-yl)-amide (3R,S)-3-(4-Fluoro-phenoxy)-pyrrolidine-1-sulfonic acid ((3R,S)-1-benzyloxy-2-oxo-pyrrolidin-3-yl)-amide (60 mg; 0.13 mmol) was dissolved in MeOH (10 ml). A slurry of 5% Pd/BaSO₄ (30 mg in 1 ml MeOH) was added under a stream of nitrogen. The mixture was stirred at room temperature and hydrogenated with H₂ (g) at 1 atm pressure for 1 h 30 min. The mixture was filtered through celite and the filtercake was washed with MeOH and EtOAc. The slightly yellow filtrate was evaporated, redissolved in EtOAc and evaporated onto Si-60 gel. The silica bound crude product was purified using 10 g of Si-60 gel, a gradient 100% Heptane to 100% (EtOAc+5% AcOH) during 30 min, and a flow of 20 ml/min. Fractions containing the product was evaporated to give the title compound as a colourless solid. Obtained 37 mg (79%). Note that the product is a mixture of diastereomers.

LC/MS (APCI): MH$^{30}$ =360.1 $^1$H-NMR(CD₃CN): δ 7.05+6.92 (m+m, 2H+2H, Ar—H), 5.73 (vbrs, 1H, —NH—), 4.97 (m, 1H, Ar—O—CH—), 4.06 (m, 1H, —NHCH—), 3.64+3.42 (m+m, 1H+1H, —CHCH₂N—), 3.46 (m, 2H, —CH₂N(OH)CO—), 3.44 (m, 2H, —CH₂NSO₂—), 2.47+1.91 (m+m, 1H+1H, —NHCHCH₂—), 2.29+2.12 (m+m, 1H+1H, Ar—O—CHCH₂CH₂—), 3.0–2.0 (vbrs, 1H, —OH) ppm. $^{13}$C-NMR(CD₃CN): δ (167.58+167.52), 159.56, 257.20, 154.45, 154.43, 154.41, 154.39, 129.93, 129.23, 126.26, 118.11, 118.03, 117.95, 117.00, 116.98, 116.77, 116.75, (78.04+78.02), (54.28+54.02), (53.25+53.18), (47.35+47.06), 46.55, 32.19, 26.72 ppm.

EXAMPLE 5A 3-(4-Fluoro-phenoxy)-pyrrolidine-1-sulfonic acid ((3S)-1-hydroxy-2,5-dioxo-pyrrolidin-3-yl)-amide;

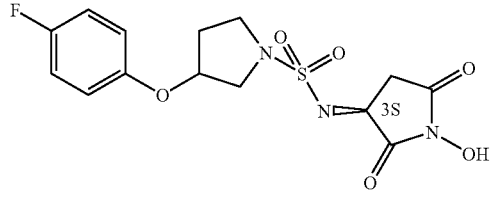

a) 3-(4-Fluoro-phenoxy)-pyrrolidine-1-sulfonic acid ((3S)-1-benzyloxy-2,5-dioxo-pyrrolidin-3-yl)-amide (3S)-3-Amino-1-benzyloxy-pyrrolidine-2,5-dione hydrochloride (192 mg; 0.75 mmol), DMAP (40 mg; 0.33 mmol), Et₃N (285 ul; 2.04 mmol) and (3R,S)-3-(4-Fluoro-phenoxy)-pyrrolidine-1-sulfonyl chloride (190 mg; 0.68 mmol) was dissolved in dry DMF (2 ml). The mixture was heated in a microwave oven at 200 W for 2×10 seconds, allowing the mixture to cool between runs. The red reaction mixture was evaporated and the residue was partitioned between EtOAc and H₂O, the organic phase was separated and washed with 3 portions of H₂O, the water phase was then extracted once with EtOAc. The combined organic phases were dried (Na₂SO₄), filtered and evaporated. The crude product was purified on Si-60 gel using EtOAc:isoHexane (1:2) as first eluent and then EtOAc:isoHexane (1:1). The fractions containing the product was evaporated to give the title compound, obtained 126 mg (40% yield). Purity >95%.

LC/MS(APCI): MH$^{30}$ =464.1 $^1$H-NMR(CD₃CN): δ 7.50+7.42 (m+m, 2H+3H, Ar—H), 7.05+6.91 (m+m, 2H+2H, Ar—H), 5.84 (brs, 1H, —NH—), 5.04 (s, 2H, Ar—CH₂O—)4.96 (m, 1H, ArOCH—), 4.40 (ddd, 1H, —NHCH—), 3.61+3.46 (m+m, 1H+3H, —N(CH₂—)₂—), 3.10+2.66 (ddd+ddd, 1H+1H, —CH₂CON—), 2.25 (m, 2H, —NCH₂CH₂—) ppm. $^{13}$C-NMR(CD₃CN): δ (169.12+169.05), (167.85+167.83), (157.61+155.25), (152.32+152.30+152.28), 132.93, 128.80, 128.32, 127.63, (116.30+116.14+116.09+116.06), (115.08+115.07+114.85+114.84), 77.71, (75.97+75.94), (52.42+52.21), (48.45+48.41), (45.49+45.25), (33.61+33.59), (30.27+30.24) ppm.

note that it is a mixture of diastereomers, hence the doubletts in the $^{13}$C-NMR experiment.

b) 3-(4-Fluoro-phenoxy)-pyrrolidine-1-sulfonic acid ((3S)-1-hydroxy-2,5-dioxo-pyrrolidin-3-yl)-amide (3R,S)-3-(4-Fluoro-phenoxy)-pyrrolidine-1-sulfonic acid ((3S)-1-benzyloxy-2,5-dioxo-pyrrolidin-3-yl)-amide (106 mg; 0.23 mmol) was dissolved in a warm mixture of MeOH (5 ml) and EtOAc (10 ml) and allowed to cool. A slurry of 10% Pd/C (30 mg) in MeOH (1 ml) was added under a stream of nitrogen. The mixture was hydrogenated using H₂ at 1 atm. pressure at room temperature for 1 h. The mixture is filtered through celite and the filtercake was washed with EtOAc, MeOH and DCM. The filtrate was evaporated, dissolved in EtOAc and filtered again through celite using EtOAc as washing solvent. This crude product was pure by NMR but was red in colour, most likely Pd residues. To remove the coloured impurities the product was further purified by filtration through a silica gel using EtOAc+1% AcOH as eluent, then by flash chromatography using 10 g of Si-60 gel and a gradient of 100% Heptane to 100% EtOAc, 44 min gradient time, followed by 100% EtOAc+1% AcOH for 20 min, flow=10 ml/min. Evaporation of solvent and finally addition of DCM gives a colourless gel, careful evaporation of solvent and finally drying under vacuum gives the title compound as a colourless solid. Obtained 64 mg (74% yield) Purity 95% by NMR and LC/MS analysis.

LC/MS (APCI): MH$^+$=374.1 $^1$H-NMR(CD₃CN): δ 8.17 (vbrs, 1H, —OH), 7.06+6.93 (m+m, 2H+2H, Ar—H), 5.82 (brd, 1H, —NH—), 4.98 (m, 1H, ArOCH—), 4.40 (m, 1H, —NHCH—), 3.61+3.45 (m+m, 1H+3H, —N(CH₂—)₂—), 3.08+2.63 (ddd+ddd, 1H+1H, —COCH₂—), 2.26+2.14 (m+m, 1H+1H, —N(CH₂CH₂—)₂—) ppm.

EXAMPLE 5B 3-(4-Fluoro-phenoxy)pyrrolidine-1-sulfonic acid ((3R)-1-hydroxy-2,5-dioxo-pyrrolidin-3-yl)-amide

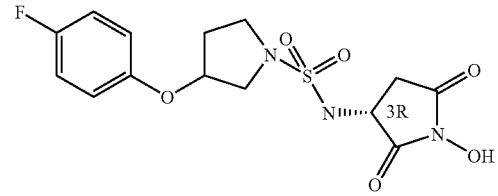

a) 3-(4-Fluoro-phenoxy)-pyrrolidine-1-sulfonic acid ((3R)-1-benzyloxy-2,5-dioxo-pyrrolidin-3-yl)-amide (3R)-3-Amino-1-benzyloxy-pyrrolidine-2,5-dione hydrochloric acid (102 mg; 0.40 mmol), DMAP (25 mg; 0.20 mmol), Et$_3$N (180 ul; 1.3 mmol) and (3R,S)-3-(4-Fluoro-phenoxy)-pyrrolidine-1-sulfonyl chloride (140 mg; 0.50 mmol) was dissolved in dry DMF (1 ml). The mixture was heated in a microwave oven at 200 W for 10 seconds. Another portion of sulfonyl chloride (140 mg; 0.50 mmol) and Et$_3$N (180 ul; 1.3 mmol) in DMF (1 ml) was added and the mixture heated again in a microwave oven at 200 W for 10 seconds. This solution was evaporated together with silica gel and purified on a Si-60 gel column using a gradient of 100% Heptane to 100% EtOAc, gradient time 44 min, 20 ml/min. The fractions containing the product was further purified using a semipreparative HPLC system on a C-18 column with a H$_2$O/MeCN+0.1% TFA solvent system. The fractions containing the product was evaporated to remove MeCN, the resulting precipitated product was extracted from the aq. phase with EtOAc. The org phase was dried (Na$_2$SO$_4$), filtered and evaporated to give the title compound as a colourless solid. Obtained 98 mg (52%).

LC/MS(APCI):=464.1 $^1$H-NMR(CD$_3$CN): δ δ 7.49+7.41 (m+m, 2H+3H, Ar—H), 7.05+6.92 (m+m, 2H+2H, Ar—H), 5.82 (brd, 1H, —NH—), 5.03 (s, 2H, Ar—CH$_2$O—), 4.96 (m, 1H, ArOCH—), 4.39 (m, 1H, —NHCH—), 3.59+3.44 (m+m, 1H+3H, —N(CH$_2$—)$_2$—), 3.08+2.64 (ddd+ddd, 1H+1H, —CH$_2$CON—), 2.24+2.13 (m+m, 1H+1H, —NCH$_2$CH$_2$—) ppm.

b) 3-(4-Fluoro-phenoxy)-pyrrolidine-1-sulfonic acid ((3R)-1-hydroxy-2,5-dioxo-pyrrolidin-3-yl)-amide Was prepared in a similar manner as described for (3R,S)-3-(4-Fluoro-phenoxy)-pyrrolidine-1-sulfonic acid ((3S)-1-hydroxy-2,5-dioxo-pyrrolidin-3-yl)-amide, using (3R,S)-3-(4-Fluoro-phenoxy)-pyrrolidine-1-sulfonic acid and ((3R)-1-benzyloxy-2,5-dioxo-pyrrolidin-3-yl)-amide (70 mg; 0.15 mmol) as starting materials.

Obtained 40 mg (71% yield) of the title compound as a colourless solid. Purity 95% by NMR and LC/MS analysis. LC/MS(APCI): MH$^{30}$ =374.1 $^1$H-NMR(CD$_3$CN): δ 7.06+6.93 (m+m, 2H+2H, Ar—H), 5.82 (brs, 1H, —NH—), 4.98 (brm, 1H, ArOCH—), 4.40 (brm, 1H, —NHCH—), 3.61+3.45 (m+m, 1H+3H, —N(CH$_2$—)$_2$—), 3.08+2.63 (ddd+ddd, 1H+1H, —COCH$_2$—), 2.26+2.14 (m+m, 1H+1H, —N(CH$_2$CH$_2$—)—), 2.3 (vvbrs, —OH) ppm. $^{13}$C-NMR (CD$_3$CN): δ (171.22+171.19), (170.18+170.17), (159.58+157.25), (154.35+154.33+154.31), (118.14+118.08+118.06+118.00), (117.01+116.99+116.77+116.76), 78.00, (54.34+54.15), (50.41+50.36), (47.39+47.18), (35.43+35.42), (32.17+32.14) ppm.

EXAMPLE 6A 4-(4-Trifluoromethyl-phenyl)-piperazine-1-sulfonic acid ((3S)-1-hydroxy-2,5-dioxo-pyrrolidin-3)amide;

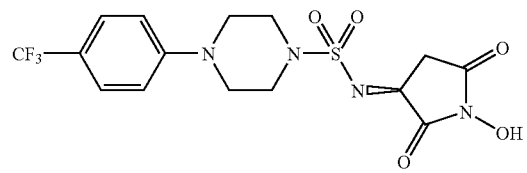

a) 4-(4Trifluoromethyl-phenyl)-piperazine-1-sulfonic acid ((3S)-1-benzyloxy-2,5-dioxo-pyrrolidin-3-yl)-amid 4-(4-Trifluoromethyl-phenyl)-piperazine-1-sulfonyl chloride (256 mg; 0.78 mmol), (3S)-3-Amino-1-benzyloxy-pyrrolidine-2,5-dione hydrochloric acid (112 mg; 0.44 mmol), Et$_3$N (230 ul; 1.65 mmol) and DMAP (43 mg; 0.35 mmol) was dissolved in DMF (2 ml). The mixture was heated in a microwave oven at 200 W for 2×10 seconds, allowed to cool to room temperature and then heated for another 10 seconds at 200 W. Evaporation of solvent and the residue was partitioned between EtOAc and 5% KHSO$_4$, separation. Organic phase were washed with H$_2$O and brine, the combined waterphases was extracted twice with warm DCM. Organic phases were combined and evaporated directly onto Si-60 gel. Purified by flash chromatography on 20 g of Si-60 gel using a gradient solvent system of 100% iso-Hexane to 100% EtOAc. Fractions containing the product was evaporated to give the title compound as a slightly yellow solid. Obtained 78 mg (35% yield). Purity by H-nmr was 90%, considered pure enough to use in next step.

LC/MS(APCI): MH$^{30}$ =513.1 $^1$H-NMR(CD$_3$CN): δ 7.55+7.06 (d+d, 2H+2H, Ar—H), 7.49+7.42 (m+m, 2H+3H, Ar—H), 5.84 (brs, 1H, —NH—), 5.05 (s, 2H, ArCH$_2$O—), 4.40 (m, 1H, —NHCH—), 3.38+3.34 (m+m, 4H+4H, —N(CH$_2$CH$_2$—)$_2$—), 3.12+2.67 (dd+dd, 1H+1H, —COCH$_2$—) ppm. $^{13}$C-NMR(CD$_3$CN): δ 170.97, 169.62, 154.20, 134.89, 130.69, 130.21, 129.52, (127.34+127.30+127.27+127.23), (124.62*), (128.98+120.66*) 116.02, 79.61, 50.38, 48.21, 46.50, 35.54 ppm.
*) Not all of the signals with C-F-coupling in Ar and CF$_3$ system can be observed.

b) 4-(4-Trifluoromethyl-phenyl)-piperazine-1-sulfonic acid ((3S)-1-hydroxy-2,5-dioxo-pyrrolidin-3-yl)-amide 4-(4Trifluoromethyl-phenyl)-piperazine-1-sulfonic acid ((3S)-1-benzyloxy-2,5-dioxo-pyrrolidin-3-yl)-amid (67 mg; 0.13 mmol) was dissolved in EtOAc (4 ml) +MeOH (4 ml). A slurry of 10% Pd/C (30 mg) in MeOH (1 ml) was added under a stream of nitrogen. The mixture was hydrogenated at room temperature at 1 atm. pressure of H$_2$ for 1 h. The reaction mixture was filtered through celite and the filtercake was washed with EtOAc and MeOH. The filtrate was evaporated and the crude product were purified twice by flash chromatography on Si-60-gel using EtOAc:Heptane (1:1) as eluent 1 to remove impurities, and EtOAc to elute the product. The fractions containing the product is evaporated and the residue is triturated with Et$_2$O, the resulting colourless solid was dried to give the title compound. Obtained 20 mg (36% yield) of the title compound.

LC/MS(APCI): MH$^+$=423.1 $^1$H-NMR(DMSO-D6): δ 10.93 (vbrs, 1H, —NO$\underline{H}$), 7.97 (brs, 1H, —N$\underline{H}$—), 7.53+7.11 (d+d, 2H+2H, Ar—$\underline{H}$), 4.46 (brm, 1H, —COC$\underline{H}$—), 3.38+3.23 (m+m, 4H+4H, —N(C$\underline{H}_2$—)—×4), 3.06+2.53 (dd+dd, 1H+1H, —COC$\underline{H}$2—) ppm.

EXAMPLE 6B 4-(4-Trifluoromethyl-phenyl)-piperazine-1-sulfonic acid ((3R)-1-hydroxy-2,5-dioxo-pyrrolidin-3-yl)-amide

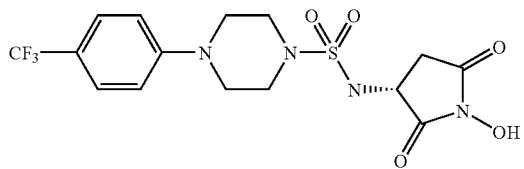

b) 4-(4Trifluoromethyl-phenyl)-piperazine-1-sulfonic acid ((3R)-1-benzyloxy-2,5-dioxo-pyrrolidin-3-yl)-amide 4-(4-Trifluoromethyl-phenyl)-piperazine-1-sulfonyl chloride (164 mg; 0.50 mmol), (3R)-3-Amino-1-benzyloxy-pyrrolidine-2,5-dione hydrochloric acid (102 mg; 0.40 mmol), Et$_3$N (180 ul; 1.30 mmol) and DMAP (25 mg; 0.20 mmol) was dissolved in DMF (1 ml). The mixture was heated in a microwave oven at 200 W for 10 seconds and allowed to cool to room temperature. Another portion of the sulfonyl chloride (164 mg; 0.50 mmol) and Et$_3$N (180 ul; 1.30 mmol) in DMF (1 ml) was added followed by heating for 10 seconds at 200 W. Reaction mixture were evaporated and filtered through Si-60 gel with EtOAC:Heptane as eluent. This crude product was purified on a C-18 column with an HPLC system using a gradient: 70% (H$_2$O+0.1% TFA):30% (MeCN+0.1% TFA) to 100% (MeCN+0.1% TFA), gradient time=35 min, flow=10 ml/min, UV=220 nm. Fractions containing the product was evaporated to a small volume, the water phase was neutralised with 5% NaHCO$_3$ and the product was extracted with EtOAc. The organic phase was dried (Na$_2$SO4), filtered and evaporated to give the title compound as a colourless solid. Obtained 94 mg (45%)

Purity by NMR>98% LC/MS(APCI):MH$^{30}$ =513.1 $^1$H-NMR(CD$_3$CN): δ 7.55+7.06 (d+d, 2H+2H, Ar—$\underline{H}$), 7.49+7.42 (m+m, 2H+3H, Ar—$\underline{H}$), 5.90 (brs, 1H, —NH—), 5.05 (brs, 2H, ArC$\underline{H}_2$O—), 4.41 (m,1H, —NHC$\underline{H}$—), 3.38+3.33 (m+m, 4H+4H, —N(C$\underline{H}_2$C$\underline{H}_2$—)$_2$—), 3.12+2.67 (dd+dd, 1H+1H, —COC$\underline{H}_2$—) ppm.

b) 4-(4-Trifluoromethyl-phenyl)-piperazine-1-sulfonic acid ((3R)-1-hydroxy-2,5-dioxo-pyrrolidin-3-yl)-amide 4-(4Trifluoromethyl-phenyl)-piperazine-1-sulfonic acid ((3R)-1-benzyloxy-2,5-dioxo-pyrrolidin-3-yl)-amid (76 mg; 0.15 mmol) was dissolved in EtOAc (5 ml)+MeOH (5 ml). A slurry of 10% Pd/C (35 mg) in MeOH (1 ml) was added under a stream of nitrogen. The mixture was hydrogenated at room temperature at 1 atm. pressure of H$_2$ for 1 h. The reaction mixture was filtered through celite and the filtercake was washed with EtOAc and MeOH. Evaporation of solvent, the crude product was purified by flash chromatograohy through 10 g of Si-60-gel using a gradient of 100% Heptane to 100% (EtOAc+1% AcOH), gradient time=30 min, then isocratic system 100% (EtOAc+1% AcOH) for 15 min. flow=20 ml/min. The fractions containing the product was evaporated and the residue was triturated with Et$_2$O and the resulting colourless solid was dried to give the title compound. Obtained 47 mg (74% yield) of the title compound.

LC/MS(APCI): MH$^{30}$ =423.1 $^1$H-NMR(CD$_3$CN): δ 7.55+7.06 (d+d, 2H+2H, $^3$J=8.8 Hz, Ar—$\underline{H}$), 5.91 (vbrs, 1H, —N$\underline{H}$—), 4.41 (brm, 1H, —COC$\underline{H}$—), 3.39+3.33 (m+m, 4H+4H, —N(C$\underline{H}_2$—)—×4), 3.10 (dd, 1H, $^2$J=17.6 Hz, $^3$J=9.1 Hz, —COC$\underline{H}$'H"—), 2.65 (dd, 1H, $^2$J=17.7 Hz, $^3$J=5.2 Hz, —COCH'$\underline{H}$"—), 2.25 (vvbrs, 1H, —NO$\underline{H}$) ppm. $^{13}$C-NMR(CD$_3$CN): δ 171.00, 169.91, 154.16, 127.27, 127.24, 127.20, 127.16, 124.58, 121.17, 120.84, 120.53, 120.20, 115.94, 110.76, 50.30,48.12, 46.44,35.31 ppm.

EXAMPLE 7

N-[(3S)-1-hydroxy-2,5-dioxopyrrolidinyl][1,1'-biphenyl]-4-sulfonamide

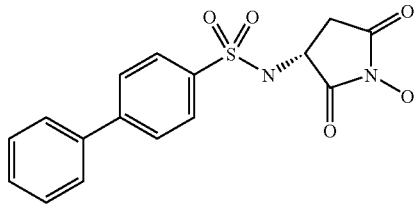

a) N-[1-(benzyloxy)-2,5-dioxo-3-(R)-pyrrolidinyl]-(1,1'-biphenyl)-4-sulfonamide

R-3-amino-1-(benzyloxy)-2,5-pyrrolidinedione hydrochloride (0.4 mmol), was dissolved in dichloromethane (2 ml) and 0.2 ml (1.2 mmol) of triethylamine was added, followed by 4-Phenylbenzenesulfonylchloride (0.2 mol) .The mixture was stirred overnight at RT,evaporated and triturated with ethyl acetate (5 ml).The precipitate was filtered and washed with small amount of ethyl acetate,the filtrate was flashed through 25 g of SiO2 (eluted with ethyl acetate),and evaporated. was used in the above general procedure.

MS:m/z=437.1 1H NMR: (chloroform/methanol): 2.65 m (2H), 4.25 m (0.94H), 4.85 s (1.95H), 7.4 m (6H), 7.65 m (2H), 7.70 d (2H), 7.85 d(2H), 7.90 d(2H)

b) N-[(3S)-1-hydroxy-2,5-dioxopyrrolidinyl][1,1'-biphenyl]-4-sulfonamide

N-[1-(benzyloxy)-2,5-dioxo-3-(R)-pyrrolidinyl][1,1'-biphenyl]4-sulfonamide was hydrogenated over 10% Pd on charcoal in ethanol+10% AcOH under normal atmosptieric pressure in the standard hydrogenation apparatus and the reaction progress was monitored by TLC. Then,the catalysator was filtered,washed with ethanol and the title compound was purified by silica gel chromatography (EtOAc+10% MeOH+1% AcOH)

MS:m/z=346.1 1H NMR: (MeOH): 3.60 m(1.5H), 3.95 m (0.6H), 4.15 m (1H), 7.3 m (4.5H), 7.65 d(2.1H), 8.15 d (2H)

EXAMPLE 8

4-(4-fluorophenoxy)-N-[(3S)-1-hydroxy-2,5-dioxopyrrolidinyl]benzenesulfonamide

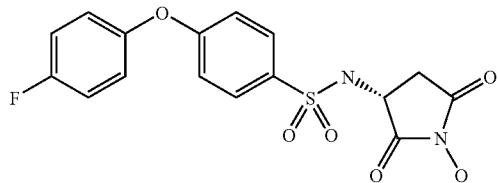

a) N-[1-(benzyloxy)-2,5-dioxo-3-(R)-pyrrolidinyl]-4-(4-fluorophenoxy)-benzenesulfonamide R-3-amino-1-(benzyloxy)-2,5-pyrrolidinedione hydrochloride from example 7b, (0.4 mmol), was dissolved in dichloromethane (2 ml) and 0.2 ml (1.2 mmol) of triethylamine was added, followed by 4-(4'-Fluorophenoxy)-benzensulfonyl chloride (0.2 mol). The mixture was stirred overnight at RT,evaporated and triturated with ethyl acetate (5 ml). The precipitate was filtered and washed with small amount of ethyl acetate,the filtrate was flashed through 25 g of SiO2 (eluted with ethyl acetate),and evaporated.

MS: m/z=528.1 1H NMR (chloroform-methanol): 2.55 m (2H), 3.95 m (1H), 5.0 s (2H), 7.25 m (5H), 7.55 d (2H), 7.65 d (2H), 7.90 d (2H), 8.15 d (2H)

b) 4-(4-fluorophenoxy)-N-[(3)-1-hydroxy-2,5-dioxopyrrolidinyl]benzenesulfonamide N-[1-(benzyloxy)-2,5-dioxo-3-(R)-pyrrolidinyl]-4-(4'-fluorophenoxy)benzenesulfonamide was hydrogenated over 10% Pd on charcoal in ethanol+10% AcOH under normal atmostperic pressure in the standard hydrogenation apparatus and the reaction progress was monitored by TLC.Then, the catalysator was filtered, washed with ethanol and the title compound was purified by silica gel chromatography (EtOAc+10% MeOH+1% AcOH).

MS:m/z=380.1 1H NMR (MeOH): 2.6 m (0.95H), 3.0 m (0.99H), 4.5 m (1H), 6.95 m (6.45H), 7.30 d (2.04H)

EXAMPLE 9

4-(4-fluorophenyl)-N-[(3S)-1-hydroxy-2,5-dioxopyrrolidinyl]-1-piperidinesulfonamide

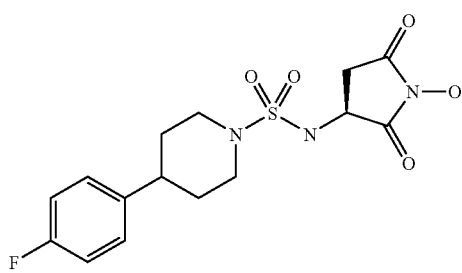

a) N-[1-(benzyloxy)-2,5-dioxo-3-pyrrolidinyl]-4-(4-fluorophenyl)-1-piperidinesulfonamide R-3-amino-1-(benzyloxy)-2,5-pyrrolidinedione hydrochloride (0.59 mmol) was dissolved in 2 ml DMF and diisopropyl ethyl amine (0.3 ml, 0.3 mmol) were added followed by 100 mg of 4-(4-fluorophenyl)-piperidine sulfonylchloride (made in Example 3) and the mixture was stirred and heated at 60 C for 48 hrs in the inert atmosphere. Then, it was evaporated, triturated with ethyl acetate, filtered, the precipitate on the filter was washed with small amount of ethyl acetate, filtrate was chromatographed on 50 g SiO2, eluted with dichloromethane and then dichloromethane+ 15% MeOH. The appropriate fraction was recrystallised from TBME-MeOH to yield 20 mg of the title compound.

MS:m/z=463.1 1H NMR: (chloroform-methanol): 2.05 m (3.1H), 2.65 m(0.8H), 3.85 m(5.1H), 4.5 m(1.5H), 5.15 s(2.1H), 6.55 d(2.1H), 7.15 dd(1.8H), 7.85 m(5H)

b) 4-(4fluorophenyl)-N-[(3S)-1-hydroxy-2,5-dioxopyrrolidinyl]-1-piperidinesulfonamide N-[1-(benzyloxy)-2,5-dioxo-3-pyrrolidinyl]4-(4fluorophenyl)-1-piperidinesulfonamide was hydrogenated over 10% Pd on charcoal in ethanol+10% AcOH under normal atmostperic pressure in the standard hydrogenation apparatus and the reaction progress was monitored by TLC. Then, the catalysator was filtered, washed with ethanol and the title compound was purified by silica gel chromatography (EtOAc+10% MeOH+1% AcOH).

MS: m/z=372.1 1H NMR: (MeOH/DMSO): 1.80 m (3.55H), 2.6 m(1.75H), 12.95 m(1.85H), 3.10 q(0.95H), 3.30 m (dd, 1H), 3.35 d(1.05H), 4.5 m (1H), 7.0 dd(1.9H), 7.25 dd(1.95H)

EXAMPLE 10

4-Butoxy-N-(1-hydroxy-2,5-dioxo-pyrrolidin-3(S)-yl)-benzenesulfonamide

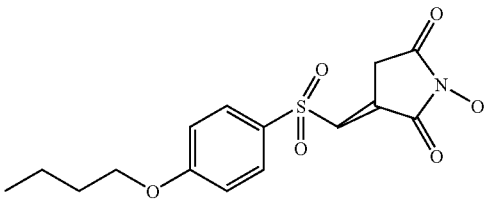

a) N-(1-Benzyloxy-2,5-dioxo-pyrrolidin-3(S)-yl)-4butoxy-benzenesulfonamide 4-(N-butoxy)benzenesulfonyl chloride (107 mg, 0.43 mmol) and S-3-amino-1-(benzyloxy)-2,5-pyrrolidinedione hydrochloride (100 mg, 0.43 mmol), was stirred in pyridine (1 mL) at room temperature for 0.5 h. The solvent was removed in vacuo and 109 mg (65%) of the sub-title compound precipitated when cold methanol (2 mL) was added.

$^1$H NMR (400 MHz, CDCl$_3$) δ 7.81 to 7.77 (2 H); 7.45 to 7.34 (3 H); 7.01 to 6.97 (2 H); 5.27 (1H, bd, NH); 5.08 (2H, s, CH$_2$Ph); 4.06 to 4.01 (3H); 3.02 (1H, dd); 2.73 (1H, dd); 1.84 to 1.77 (2H, m, CH$_2$); 1.56 to 1.47 (2H, m, CH$_2$); 1.00 (3H, t, CH$_3$). APCI-MS m/z: 433 [MH+].

b) 4-Butoxy-N-(1-hydroxy-2,5-dioxo-pyrrolidin-3 (S)-yl)- benzenesulfonamide

N-(1-Benzyloxy-2,5-dioxo-pyrrolidin-3(S)-yl)-4-butoxy-benzenesulfonamide (100 mg, 0,23 mmol) was hydrogenated at atmospheric pressure for 1 h in ethyl acetate/methanol (1:1, 4 mL) with palladium on activated charcoal (50 mg, 10%). The mixure was filtered through Celite® and concentrated. The residue was purified by silica gel chromatography (ethyl acetate-acetic acid, 100:2) to give 59 mg (75%) of the title compound.

$^1$H NMR (400 MHz, CD$_3$CN) δ 7.81 to 7.77 (2H); 7.08 to 7.04 (2H); 6.01 (1H, bd, NH); 4.33 to 4.26 (1H, m); 4.11 to 4.04 (2H); 2.85 (1H, dd); 2.39 (1H, dd); 1.82 to 1.74 (2H, m, CH$_2$); 1.55 to 1.45 (2H, m, CH$_2$); 1.21 (3H, t, CH$_3$). APCI-MS m/z: 343 [MH+].

EXAMPLE 11

The following compounds were prepared essentially as described in Example 10:

a) 4-Butoxy-N-(1-hydroxy-2,5-dioxo-pyrrolidin-3 (R)-yl)- benzenesulfonamide

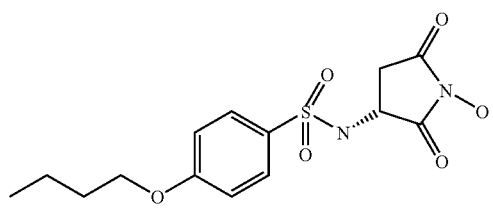

$^1$H NMR (400 MHz, CD$_3$CN) δ 7.81 to 7.77 (2H); 7.08 to 7.04 (2H); 6.01 (1H, bd, NH); 4.33 to 4.26 (1H, m); 4.11 to 4.04 (2H); 2.85 (1H, dd); 2.39 (1H, dd); 1.82 to 1.74 (2H, m, CH$_2$); 1.55 to 1.45 (2H, m, CH$_2$); 1.21 (3H, t, CH$_3$). APCI-MS m/z: 343 [MH+].

b) Naphthalene-2-sulfonic acid (1-hydroxy-2,5-dioxo-pyrrolidin-3(S)-yl)-amide

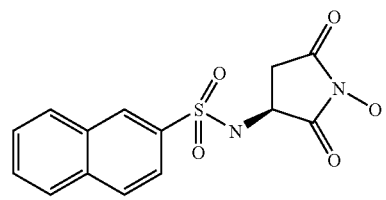

$^1$H NMR (400 MHz, CD$_3$CN) δ8.51 to 8.48 (1H); 8.12 to 8.01 (3H); 7.89 to 7.85 (1H); 7.74 to 7.65 (2H); 6.36 (1H, NH); 4.38 (1H, m); 2.85 (1H, dd); 2.41 (1H, dd).

EXAMPLE 12

Biphenyl-4-sulfonic acid [(3R)-(1-hydroxy-2-oxo-pyrrolidin-3-yl]-amide

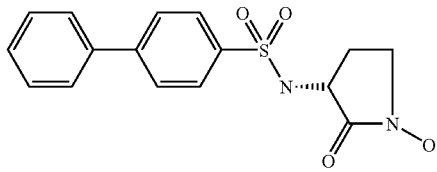

a) Biphenyl-4-sulfonic acid [(3R)- (1-bezyloxy-2-oxo-pyrrolidin-3-yl]-amide (3R)-3-Amino-1-benzyloxy-pyrrolidin-2-one trifluoroacetate (71 mg, 0.22 mmol) (EP0318 091AR) was added to dichloromethane (20 ml) and diisopropyl ethylamine (113 ul, 0.66 mmol). Biphenyl-4-sulfonyl chloride was added and the mixture stirred at room temperature for 1 hour. The solution was washed with water (2×15 ml), dried with sodium sulphate to give 82 mg (87%) on evaporation.

$^1$H NMR CDCl$_3$: δ 1.94–2.05 (1H, m); 2.43–2.50 (1H, m); 3.16–3.25 (2H, m); 3.67 (1H, dt); 4.95 (1H, s); 5.17 (1H, d); 7.36–7.43 (5H, m); 7.47 (2H, t); 7.59 (2H, d); 7.72 (2H, d); 7.94 (2H, d) APCI-MS r/z:423 [MH+].

b) Biphenyl-4-sulfonic acid [(3R)- (1-hydroxy-2-oxo-pyrrolidin-3-yl]-amide

Biphenyl-4-sulfonic acid [(3R)- (l-hydroxy-2-oxo-pyrrolidin-3-yl]-amide (100 mg, 0,23 mmol) was hydrogenated at atmospheric pressure for 1 hour in methanol (20 mL) with palladium on barium sulphate (50 mg, 100%). The mixure was filtered through Celite® and concentrated. The residue was purified by silica gel chromatography (ethyl acetate-acetic acid, 100:2) to give 54 mg (66%) of the title compound.

$^1$H NMR DMSOD$_6$: δ 1.54–1.63 (1H, m); 2.01–2.09 (1H, m); 3.26–3.33 (1H, m); 3.98 (1H, t); 7.43 (1H, t); 7.50 (2H, t); 7.73 (1H, d); 7.89 (4H, abq); 9.8 (1H, brs) APCI-MS m/z: 333 [MH+].

EXAMPLE 13

(3R)-N-(1-Hydroxy-2-oxo-pyrrolidin-3-yl)-4-trifluoromethoxy-benzenesulfonamide

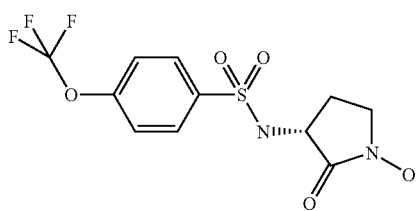

a) (3R)-N-(1-Benzyloxy-2-oxo-pyrrolidin-3-yl)-4-trifluoromethoxy-benzenesulfonamide The intermediate sulfonamide was prepared as in example 13a using 4-trifluoromethoxy sulfonyl chloride, yield 121 mg (99%) of the sub-title compound. APCI-MS m/z: 431 [MH+].

b) (3R)-N-(1-Hydroxy-2-oxo-pyrrolidin-3-yl)-4-trifluoromethoxy-benzenesulfonamide Hydrogenolysis as in example 13 yielded 56 mg (58%) of the title compound.

$^1$H NMR DMSOD$_6$: δ 1.85–1.95 (1H, m); 2.10–2.17 (1H, m); 3.52 (1H, q); 3.69 (1H, t); 4.18 (1H, brd); 6.95 (1H, brd, NH); 7.37 (2H, d); 8.05 (2H, d) APCI-MS m/z: 341 [MH+].

EXAMPLE 14

(3R)-4-(4-Fluoro-phenoxy)-N-(1-hydroxy-2-oxo-pyrrolidin-3-yl)-benzenesulfonamide

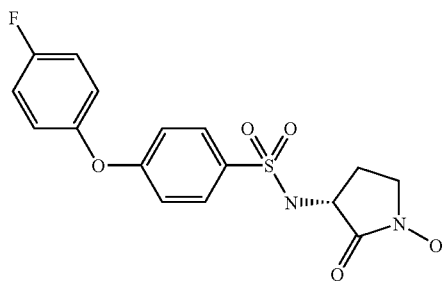

a) (3R)-4-(4-Fluoro-phenoxy)-N-(1-benzyloxy-2-oxo-pyrrolidin-3-yl)-benzenesulfonamide The intermediate sulfonamide was prepared as in example 13a by using the appropiate sulfonyl chloride to yield 136 mg (99%) APCI-MS m/z: 457 [MH+].

b) (3R)-4(4-Fluoro-phenoxy)-N-(1-hydroxy-2-oxo-pyrrolidin-3-yl)-benzenesulfonamide Hydrogenolysis to the title compound as in example 13 yielded 68 mg (62%)

$^1$H NMR DMSOD$_6$: δ 1.91–2.01 (1H, m); 2.13–2.21 (1H, m); 3.52 (1H, q); 3.70 (1H, t); 4.09 (1H, t); 7.00–7.13 (6H, m); 7.90 (2H, d) APCI-MS m/z: 431 [MH+].

EXAMPLE 15

(3)4'-Trifluoromethyl-biphenyl-4-sulfonic acid (1-hydroxy-2-oxo-pyrrolidin-3-yl)-amide

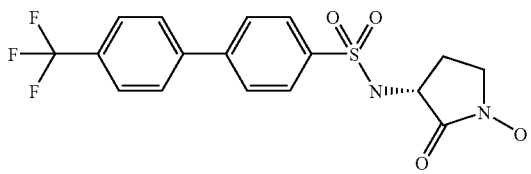

a) (3)-4'-Trifluoromethyl-biphenyl-4-sulfonic acid (1-benzyloxy-2-oxo-pyrrolidin-3-yl)-amide The intermediate sulfonamide was prepared as in example 13a by using the appropiate sulfonyl chloride to yield 106 mg (83%) APCI-MS m/z: 491 [MH+].

b) (3)4'-Trifluoromethyl-biphenyl-4-sulfonic acid (1-hydroxy-2-oxo-pyrrolidin-3-yl)-amide Hydrogenolysis to the title compound as in example 13 yielded 50 mg (58%)

$^1$H NMR DMSOD$_6$: δ 1.60 (1H, sext); 2.03–2.10 (1H, m); 3.27–3.32 (2H, m); 4.00 (1H, t); 7.85 (2H, d); 7.93–7.98 (6H, m); 8.28 (1H, brs); 9.78 (1H, brs) APCI-MS m/z: 401 [MH+].

EXAMPLE 16

(3R)-4'-Fluoro-biphenyl-4-sulfonic acid (1-hydroxy-2-oxo-pyrrolidin-3-yl)-amide

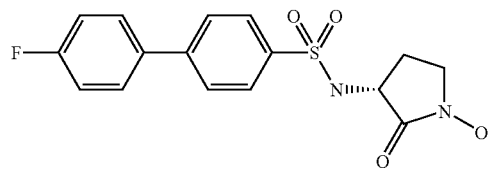

a) (3R)-4'-Fluoro-biphenyl-4-sulfonic acid (1-benzyloxy-2-oxo-pyrrolidin-3-yl)-amide The intermediate sulfonamide was prepared as in example 13a by using the appropiate sulfonyl chloride to yield 105 mg (98%)

$^1$H NMR DMSOD$_6$: δ 1.55 (1H, quint); 1.98–2.06 (1H, m); 3.23–3.27 (2H, m); 3.29 (1H, s, Under HOD peak); 4.02 (1H, t); 4.85 (2H, s); 7.30–7.40 (6H, m); 7.19 (2H, q); 7.87 (2H, q); 8.27 (1H, brs) APCI-MS m/z: 441 [MH+].

b) (3R)-4'-Fluoro-biphenyl-4-sulfonic acid (1-hydroxy-2-oxo-pyrrolidin-3-yl)-amide Hydrogenolysis to the title compound as in example 13 yielded 77 mg (92%) APCI-MS m/z: 351 [MH+].

EXAMPLE 17

(3R)-Biphenyl-4-sulfonic acid benzyl-(1-hydroxy-2-oxo-Pyrrolidin-3-yl)-amide

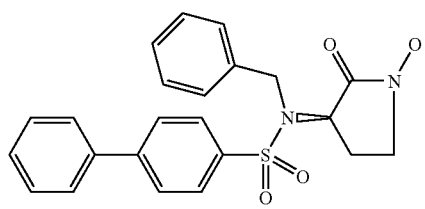

a) (3R)-Biphenyl-4-sulfonic acid benzyl-(1-hydroxy-2-oxo-pyrrolidin-3-yl)-amide

The intermediate from example 13a (126 mg, 0.30 mmol) was stirred in dimethyl formamide (3 ml) with benzyl bromide (70 μl, 0.60 mmol) and cesium carbonate (107 mg, 0.33 mmol) for 3 hours at room temperature. The solution was treated with dilute hydrochloric acid (20 ml), extracted into ethyl acetate (3×20 ml), the organic phases were combined and washed with brine, sodium sulphated dried and evaporated to give 152 mg (99%) residue. This was used in the next step with out further purification. APCI-MS m/z: 513 [MH+].

b) (3R)-Biphenyl-4-sulfonic acid benzyl-(1-hydroxy-2-oxo-pyrrolidin-3-yl)-amide

Hydrogenolysis to the title compound as in example 13 yielded 70 mg (55%)
$^1$H NMR DMSOD$_6$: δ 1.62 (1H, quint); 2.10–2.16 (1H, m, 1); 3.15 (1H, t); 3.28 (1H, q, Partially obscured by HOD); 4.32 (2H, abq); 4.64 (1H, t); 7.23–7.26 (1H, m); 7.30 (2H, t); 7.36 (2H, d); 7.44 (1H, t); 7.52 (2H, t); 7.75 (2H, d); 7.86 (2H, d); 7.98 (2H, d); 9.85 (1H, s) APCI-MS m/z: 423 [MH+].

EXAMPLE 18

(3R)-N-(1-Hydroxy-2-oxo-pyrrolidin-3-yl)-4-(4-trifluoromethyl-phenoxy)-benzenesulfonamide

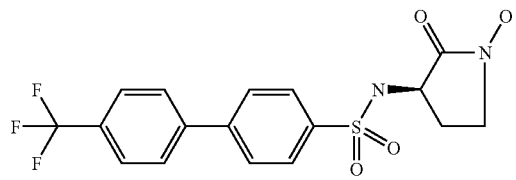

a) (3R)-N-(1-Hydroxy-2-oxo-pyrrolidin-3-yl)-4-(4-trifluoromethyl-phenoxy)-benzenesulfonamide The intermediate sulfonamide was prepared as in example 13a by using the appropiate sulfonyl chloride to yield 141 mg (75%). APCI-MS m/z: 507 [NH+].

b) (3R)-N-(1-Hydroxy-2-oxo-pyrrolidin-3-yl)-4-(4-trifluoromethyl-phenoxy)-benzenesulfonamide Hydrogenolysis to the title compound as in example 13 yielded 20 mg (23%)
$^1$H NMR DMSOD$_6$: δ 1.58 (1H, quint); 2.00–2.08 (1H, m); 3.27–3.32 (2H, m, Partially obscured by HOD); 3.95 (1H, t); 7.25 (4H, t); 7.78 (4H, abq); 8.2 (1H, brs); 9.80 (1H, brs) APCI-MS m/z: 417 [MH+].

EXAMPLE 19

(3R)-Biphenyl-4-sulfonic acid (1-hydroxy-2-oxo-pyrrolidin-3-yl)-methyl-amide

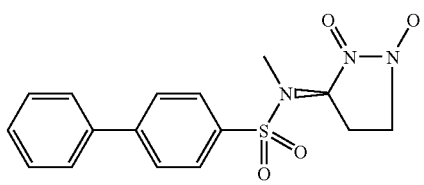

a) (3R)-Biphenyl-4-sulfonic acid (1-hydroxy-2-oxo-pyrrolidin-3-yl)-methyl-amide

The intermediate was prepared as in example 17a using methyl iodide instead of benzyl bromide to yield 150 mg (99%) APCI-MS m/z: 437 [MH+].

b) (3R)-Biphenyl-4-sulfonic acid (1-hydroxy-2-oxo-pyrrolidin-3-yl)-methyl-amide

Hydrogenolysis to the title compound as in example 13 yielded 57 mg (45%)
$^1$H NMR DMSOD$_6$: δ 1.73–1.83 (1H, m); 2.01–2.10 (1H, m); 2.64 (3H, s); 3.32–3.38 (2H, m, Partially obscured by HOD); 4.74 (1H, t); 7.44 (1H, t); 7.51 (2H, t); 7.74 (2H, d); 7.89 (4H, abq); 9.99 (1H, brs) APCI-MS m/z: 347 [MH+].

EXAMPLE 20

(3R)-4'-Trifluoromethyl-biphenyl-4-sulfonic acid (1-hydroxy-2-oxo-pyrrolidin-3-yl)-methyl-amide

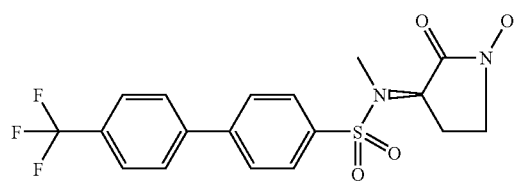

a) (3R)-4'-Trifluoromethyl-biphenyl-4-sulfonic acid (1-benzyloxy-2-oxo-pyrrolidin-3-yl)-methyl-amide The intermediate was prepared as in example 19a using the intermediate from example 15a to yield 23 mg (26%) of the sub-title compound.
APCI-MS m/z: 505 [MH+].

b) (3R)-4'-Trifluoromethyl-biphenyl-4-sulfonic acid (1-hydroxy-2-oxo-pyrrolidin-3-yl)-methyl-amide Hydrogenolysis to the title compound as in example 13 yielded 5 mg (26%) of the title compound.
$^1$H NMR DMSOD$_6$: δ 1.76–1.85 (1H, m); 2.04–2.11 (1H, m); 2.65 (3H, s); 3.37 (2H, t); 4.76 (1H, t); 7.86 (2H, d); 7.97 (6H, d); 9.90 (1H, s) APCI-MS m/z: 415 [MH+].

EXAMPLE 21

(3R)-4'-Trifluoromethyl-biphenyl-4-sulfonic acid benzyl-(1-hydroxy-2-oxo-pyrrolidin-3-yl)-amide

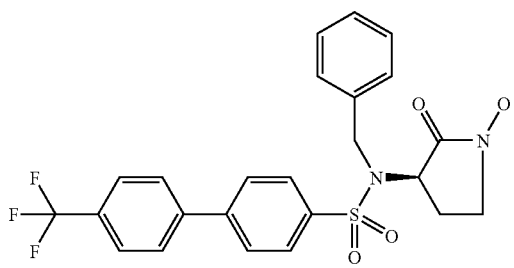

a) (3R)-4'-Trifluoromethyl-biphenyl-4-sulfonic acid benzyl-(1-benzyloxy-2-oxo-pyrrolidin-3-yl)-amide The intermediate was prepared as in example 17a using the intermediate from example 15a to yield 130 mg (98%) of the sub-title compound. APCI-MS m/z: 581 [MH+].

b) (3R)-4'-Trifluoromethyl-biphenyl-4-sulfonic acid benzyl-(1-hydroxy-2-oxo-pyrrolidin-3-yl)-amide Hydrogenolysis to the title compound as in example 13 yielded (70%).
$^1$H NMR DMSOD$_6$: δ 1.57–1.67 (1H, m); 2.10–2.17 (1H, m); 3.15 (1H, t); 3.29 (1H, q, Partially obscured by HOD); 4.33 (2H, abq, J=154,18 Hz); 4.66 (1H, t); 7.23–7.36 (5H, m); 7.87 (2H, d); 7.92–8.03 (6H, m); 9.85 (1H, s) APCI-MS m/z: 491 [MH+].

EXAMPLE 22

(3R)-Biphenyl-4-sulfonic acid (1-hydroxy-2-oxo-pyrrolidin-3-yl)-propyl-amide

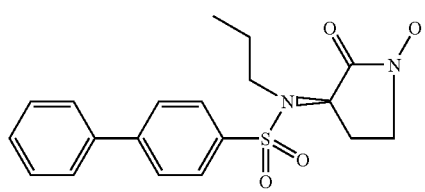

a) (3R)-Biphenyl-4-sulfonic acid (benzyloxy-2-oxo-pyrrolidin-3-yl)-propyl-amide

The intermediate was prepared as example 17a using propyl iodide instead of benzyl bromide to yield 91 mg (58%) of the sub-title compound. APCI-MS m/z: 465 [MH+].

b) (3R)-Biphenyl4-sulfonic acid (1-hydroxy-2-oxo-pyrrolidin-3-yl)-propyl-amide

Hydrogenolysis to the title compound as in example 13 yielded 25 mg (34%).
$^1$H NMR DMSOD$_6$: δ 0.78 (3H, t); 1.50–1.62 (2H, m); 1.82–1.91 (1H, m); 2.15–2.32 (1H, m); 2.90–3.06 (2H, m); 3.32–3.40 (2H, m, Partially obscured by HOD); 4.62 (1H, t); 7.44 (1H, t); 7.51 (2H, t); 7.86 (2H, d); 7.97 (2H, d); 9.86 (1H, brs) APCI-MS m/z: 375 [MH+].

EXAMPLE 23

(3R)-4'-Trifluoromethyl-biphenyl-4-sulfonic acid (1-hydroxy-2-oxo-pyrrolidin-3-yl)-propyl-amide

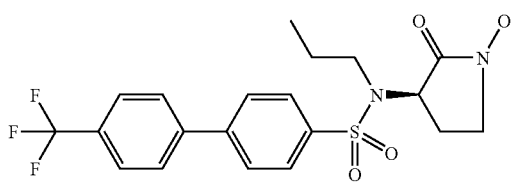

a) (3R)-4'-Trifluoromethyl-biphenyl-4-sulfonic acid (1-hydroxy-2-oxo-pyrrolidin-3-yl)-propyl-amide Was prepared as example 22a using the intermediate from example 15a to yield 135 mg (99%) of the sub-title compound. APCI-MS m/z: 533 [MH+].

b) (3R)-4'-Trifluoromethyl-biphenyl-4-sulfonic acid (1-hydroxy-2-oxo-pyrrolidin-3-yl)-propyl-amide Hydrogenolysis to the title compound as in example 13 yielded 36 mg (31%).
$^1$H NMR DMSOD$_6$: δ 0.77 (3H, t); 1.49–1.63 (2H, m); 1.80–1.93 (1H, m); 2.14–2.25 (1H, m); 2.92–3.05 (2H, m); 3.36 (2H, quint); 4.63 (1H, t); 7.85 (2H, d); 7.92–8.02 (6H, m); 9.86 (1H, s) APCI-MS m/z: 443 [MH+].

EXAMPLE 24

(3R)-4'-Trifluoromethyl-biphenyl-4-sulfonic acid (1-hydroxy-2-oxo-pyrrolidin-3-yl)-isobutyl-amide

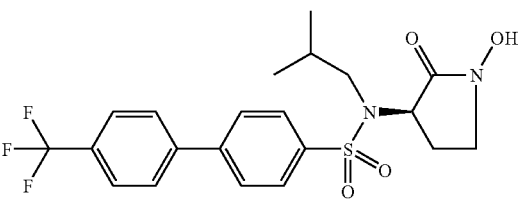

a) (3R)-4'-Trifluoromethyl-biphenyl-4-sulfonic acid (1-hydroxy-2-oxo-pyrrolidin-3-yl)-isobutyl-amide The intermediate was prepared as in example 24a using isobutyl bromide instead of propyl iodide to yield 136 mg (100%) of the sub-title compound. APCI-MS m/z: 547 [MH+].

b) (3R)-4'-Trifluoromethyl-biphenyl-4-sulfonic acid (1-hydroxy-2-oxo-pyrrolidin-3-yl)-isobutyl-amide Hydrogenolysis to the title compound as in example 13 yielded 47 mg (41%)

$^1$H NMR DMSOD$_6$: δ 0.79–0.85 (6H, m); 1.77–1.86 (1H, m); 1.86–1.96 (1H, m); 2.14–2.22 (1H, m); 2.86–2.97 (2H, m); 3.35–3.43 (2H, m); 4.59 (1H, t); 7.86 (2H, d); 7.93–8.01 (6H, m); 9.84 (1H, brs) APCI-MS m/z: 457 [MH+].

EXAMPLE 25

N-[(3R,5S)-1-(Hydroxy)-5-isopropyl-2-oxopyrrolidinyl]-4'-(trifluoromethyl)[1,1'-biphenyl]-4-sulfonamide;

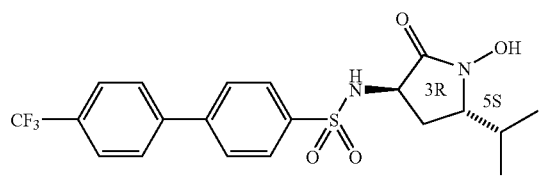

a) N-[(3R,5S)-1-(Benzyloxy)-5-isopropyl-2-oxopyrrolidinyl]-4'-(trifluoromethyl)[1,1'-biphenyl]-4-sulfonamide To a solution of (3R,5S)-3-amino-1-(Benzyloxy)-5-isopropyl-2-pyrrolidinone trifluoroacetate (0.072 g, 0.19 mmoles), triethylamine (0.13 mL, 0.93 mmoles) and dry dichloromethane (1.0 mL) was added in small portions 4'-(trifluoromethyl)[1,1'-biphenyl]-4-sulfonyl chloride (0.063 g, 0.20 mmoles) during two minutes. The mixture was stirred under dry nitrogen at 22° C. for 45 minutes, concentrated by rotary evaporation, re-dissolved in dichloromethane (2 mL), mixed with a silica (1 g), concentrated again and then applied on a silica column. Elution with ethyl acetate/n-heptane (1:4 through 1:1) and concentration of pure fractions gave 0.082 g (83% yield) of the title compound as a white solid. LC-MS (APCI) m/z 533 (M+1). $^1$H NMR (CDCl$_3$) δ 8.01 (d, J=8 Hz, 2H), 7.72 (d, J=8 Hz, 2H), 7.71 (d, J=8 Hz, 2H) 7.70 (d, J=8 Hz, 2H), 7.41–7.33 (m, 5H), 5.55 (d, J=4 Hz, 1H), 5.00 (d, J=11 Hz, 1H), 4.93 (d, J=11 Hz, 1H), 3.79 (dt, J$_1$=4 Hz, J$_2$=9 Hz; 1H), 3.37–3.31 (m, 1H), 2.29 (ddd, J$_1$=2 Hz, J$_2$=9 Hz, J$_3$=11 Hz; 1H), 2.09–1.98 (m, 2H), 0.85 (d, J=7 Hz, 3H) and 0.76 (d, J=7 Hz, 3H) ppm.

b) N-[(3R,5S)-1-(Hydroxy)-5-isopropyl-2-oxopyrrolidinyl]-4'-(trifluoromethyl)[1,1'-biphenyl]-4-sulfonamide N-[(3R,5S)-1-(Benzyloxy)-5-isopropyl-2-oxopyrrolidinyl]-4'-(trifluoromethyl)[1,1'-biphenyl]-4-sulfonamide (0.045 g, 0.084 mmoles, Example 25a) in 8.0 mL methanol was hydrogenated on 5% Pd/BaSO$_4$ (0.005 g) at 1 atm H$_2$ and 22° C. After 5 hours the solution was filtered through Celite and concentrated by rotary evaporation to afford 0.035 g of impure product (HPLC-purity: 90.5%). This was purified by semi-preparative chromatography [Kromasil™ (250 mm×20 mm) from 30 through 70% acetonitrile to water (0.1% TFA) during 35 minutes at 10 mL/min flow] to afford 0.028 g (76% yield) of the title compound as a colourless solid. LC-MS (APCI) m/z 443 (M+1). $^1$H NMR (CD$_3$OD) δ 8.04 (d, J=8 Hz, 2H), 7.89 (d, J=8 Hz, 2H), 7.88 (d, J=8 Hz, 2H) 7.79 (d, J=8 Hz, 2H), 4.04 (t, J=8 Hz; 1H), 3.36 (dt, J$_1$=3 Hz, J$_2$=9 Hz, 1H), 2.21–2.10 (m, 2H), 1.86 (ddd, J$_1$=9 Hz, J$_2$=8 Hz, J$_3$=14 Hz; 1H), 0.91 (d, J=8 Hz, 3H) and 0.80 (d, J=8 Hz, 3H) ppm.

EXAMPLE 26

N-[(3R,5R)-1-(Hydroxy)-5-isopropyl-2-oxopyrrolidinyl]-4'-(trifluoromethyl)[1,1'-biphenyl]-4-sulfonamide

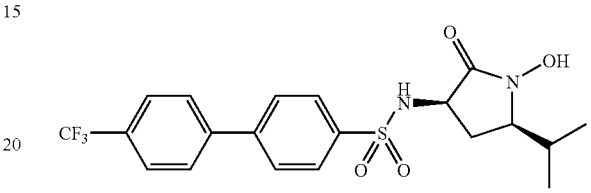

a) N-[(3R,5R)-1-(Benzyloxy)-5-isopropyl-2-oxopyrrolidinyl]-4'-(trifluoromethyl)[1,1'-biphenyl]-4-sulfonamide To a solution of (3R,5R)-3-amino-1-(Benzyloxy)-5-isopropyl-2-pyrrolidinone trifluoroacetate (0.036 g, 0.10 mmoles), triethylamine (0.070 mL, 0.50 mmoles) and dry dichloromethane (0.70 mL) was added in small portions 4'-(trifluoromethyl)[1,1'-biphenyl]-4-sulfonyl chloride (0.034 g, 0.11 mmoles) during two minutes. The mixture was stirred under dry nitrogen at 22° C. for 60 minutes, concentrated by rotary evaporation, re-dissolved in dichloromethane (2 mL), mixed with a silica (1 g), concentrated again and then applied on a silica column. Elution with ethyl acetate/n-heptane (1:4 through 1:3) and concentration of pure fractions gave 0.030 g (57% yield) of the title compound as a white solid. LC-MS (APCI) m/z 533 (M+1). $^1$H NMR (CDCl$_3$) δ 8.02 (d, J=8 Hz, 2H), 7.74 (d, J=8 Hz, 2H), 7.72 (d, J=8 Hz, 2H) 7.70 (d, J=8 Hz, 2H), 7.40–7.30 (m, 5H), 5.43 (d, J=3 Hz, 1H), 4.99 (d, J=10 Hz, 1H), 4.88 (d, J=10 Hz, 1H), 3.76 (dt, J$_1$=3 Hz, J$_2$=9 Hz, 1H), 3.31 (ddd, J$_1$=4 Hz, J$_2$=6 Hz, J$_3$=9 Hz, 1H), 2.40 (ddd, J$_1$=7 Hz, J$_2$=9 Hz, J$_3$=13 Hz, 1H), 2.20–2.08 (m, 1H), 1.76 (dt, J$_1$=9 Hz, J$_2$=13 Hz, 1H), 0.85 (d, J=7 Hz, 3H) and 0.83 (d, J=7 Hz, 3H) ppm.

b) N-[(3R,5R)-1-(Hydroxy)-5-isopropyl-2-oxopyrrolidinyl]-4'-(trifluoromethyl)[1,1'-biphenyl]-4-sulfonamide N-[(3R,5R)-1-(Benzyloxy)-5-isopropyl-2-oxopyrrolidinyl]-4'-(trifluoromethyl)[1,1'-biphenyl]-4-sulfonamide (0.030 g, 0.056 mmoles, Example 26a) in 5.0 mL methanol was hydrogenated on 5% Pd/BaSO$_4$ (0.004 g) at 1 atm H$_2$ and 22° C. After 5 hours the solution was filtered through Celite and concentrated by rotary evaporation to afford 0.024 g of impure product (HPLC-purity: 84–86%). This was purified by semi-preparative chromatography [Kromasil™ (250 mm×20 mm) from 30 through 70% acetonitrile to water (0.1% TFA) during 35 minutes at 10 mL/min flow] to afford 0.018 g (72% yield) of the title compound as a colourless solid. LC-MS (APCI) m/z 443 (M+1). $^1$H NMR (CD$_3$OD) δ 8.05 (d, J=9 Hz, 2H), 7.89 (d, J=8 Hz, 2H), 7.88

(d, J=8 Hz, 2H) 7.79 (d, J=9 Hz, 2H), 4.03 (t, J=9 Hz, 1H), 3.53 (ddd, J$_1$=4 Hz, J$_2$=6 Hz, J$_3$=9 Hz, 1H), 2.27–2.11 (m, 2H), 1.50 (dt, J$_1$=10 Hz, J$_2$=13 Hz, 1H), 0.90 (d, J=7 Hz, 3H) and 0.85 (d, J=7 Hz, 3H) ppm.

EXAMPLE 27

N-[(3R,5S)-1-(Hydroxy)-5-isopropyl-2-oxopyrrolidinyl]-N-propyl-4'-(trifluoromethyl)[1,1'-biphenyl]-4-sulfonamide;

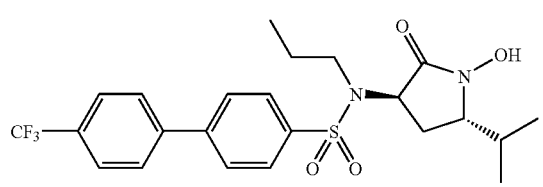

a) N-[(3R,5S)-1-(Benzyloxy)-5-isopropyl-2-oxopyrrolidinyl]-N-propyl-4'-(trifluoromethyl)[1,1'-biphenyl]-4-sulfonamide N-[(3R,5S)-1-(Benzyloxy)-5-isopropyl-2-oxopyrrolidinyl]-4'-(trifluoromethyl)[1,1'-biphenyl]-4-sulfonamide (0.047 g, 0.088 mmoles, Example 27a), 1-iodopropane (0.052 mL, 0.53 mmoles), cesium carbonate (0.043 g, 0.13 mmoles) and anhydrous N,N-dimethylformamide (0.50 mL) was stirred at 55° C. (oil temperature) over night, concentrated by rotary evaporation, taken up diethylether and washed with water once. The aqueous phase was washed with a second portion of diethylether, the combined organic phases were washed with brine, dried with potassium carbonate, filtered and concentrated by rotary evaporation. Flash chromatography of the crude product on silica using dichloromethane-methanol (99:1) as eluent gave the title compound as a colourless oil. LC-MS (APCI) m/z 575 (M+1). $^1$H NMR (CDCl$_3$) δ 8.12 (d, J=8 Hz, 2H), 7.74–7.69 (m, 5H), 7.72 (d, J=8 Hz, 2H), 7.44–7.34 (m, 4H), 5.01 (s, 2H), 4.48 (dd, J$_1$=8 Hz, J$_2$=10 Hz, 1H), 3.45 (dt, J$_1$=3 Hz, J$_2$=9 Hz, 1H), 3.10–2.98 (m, 2H), 2.24 (ddd, J$_1$=2 Hz, J$_2$=10 Hz, J$_3$=14 Hz, 1H), 2.20–2.10 (m, 1H), 2.03 (dt, J$_1$=9 Hz, J$_2$=14 Hz, 1H), 1.73–1.51 (m, 2H), 0.87 (d, J=7 Hz, 3H), 0.84 (d, J=7 Hz, 3H) and 0.82 (obscured t, J=7 Hz, 3H) ppm.

b) N-[(3R,5S)-1-(Hydroxy)-5-isopropyl-2-oxopyrrolidinyl]-N-propyl-4'-(trifluoromethyl)[1,1'-biphenyl]-4-sulfonamide N-[(3R,5S)-1-(Benzyloxy)-5-isopropyl-2-oxopyrrolidinyl]-N-propyl-4'-(trifluoromethyl)[1,1'-biphenyl]-4-sulfonamide (0.023 g, 0.040 mmoles, Example 28a) in 5.0 mL methanol was hydrogenated on 5% Pd/BaSO$_4$ (0.005 g) at 1 atm H$_2$ and 22° C. After 6 hours the solution was filtered through Celite and concentrated by rotary evaporation to afford 0.019 g (98% yield) of the title compound as a white solid. LC-MS (APCI) m/z 485 (M+1). $^1$H NMR (DMSO-d$_6$) δ 9.90 (br s, 1H), 8.04 (d, J=8 Hz, 2H), 7.99 (d, J=8 Hz, 2H), 7.97 (d, J=8 Hz, 2H), 7.88 (d, J=8 Hz, 2H), 4.53 (dd, J$_1$=8 Hz, J$_2$=10 Hz, 1H), 3.62 (dt, J$_1$=3 Hz, J$_2$=9 Hz, 1H), 3.08–2.90 (sym m, 2H), 2.14–2.02 (sym m, 2H), 1.87 (ddd, J$_1$=8 Hz, J$_2$=9 Hz, J$_3$=14 Hz, 1H), 1.67–1.49 (sym m, 2H), 0.86 (d, J=7 Hz, 3H), 0.80 (t, J=7 Hz, 3H) and 0.77 (d, J=7 Hz, 3H) ppm.

EXAMPLE 28

N-[(3R,5R)-1-(Hydroxy)-5-isopropyl-2-oxopyrrolidinyl]-N-propyl-4'-(trifluoromethyl)[1,1'-biphenyl]-4-sulfonamide

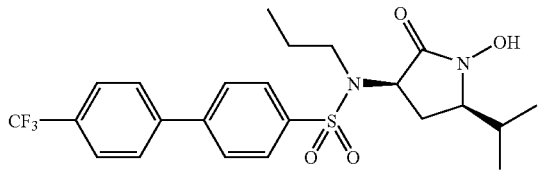

a) N-[(3R,5R)-1-(Benzyloxy)-5-isopropyl-2-oxopyrrolidinyl]-N-propyl-4'-(trifluoromethyl)[1,1'-biphenyl]-4-sulfonamide N-[(3R,5R)-1-(Benzyloxy)-5-isopropyl-2-oxopyrrolidinyl]-4'-(trifluoromethyl)[1,1'-biphenyl]-4-sulfonamide (0.030 g, 0.056 mmoles, Example 27b), 1-iodopropane (0.033 mL, 0.34 mmoles), cesium carbonate (0.028 g, 0.085 mmoles) and anhydrous N,N-dimethylformamide (0.40 mL) was stirred at 55° C. (oil temperature) over night, concentrated by rotary evaporation, taken up diethylether and washed with water once. The aqueous phase was washed with a second portion of diethylether, the combined organic phases were washed with brine, dried with potassium carbonate, filtered and concentrated by rotary evaporation. Flash chromatography of the crude product on silica using dichloromethane-methanol (99:1) as eluent gave the title compound as a colourless oil. LC-MS (APCI) m/z 575 (M+1). $^1$H NMR (CDCl$_3$) δ 8.10 (d, J=9 Hz, 2H), 7.73 (d, J=9 Hz, 2H), 7.72 (app s, 5H), 7.43–7.34 (m, 4H), 5.09 (d, J=10 Hz, 1H), 4.92 (d, J=10 Hz, 1H), 4.54 (t, J=10 Hz, 1H), 3.34 (ddd, J$_1$=4 Hz, J$_2$=6 Hz, J$_3$=10 Hz, 1H), 3.12 (t, J=8 Hz, 2H), 2.30 (ddd, J$_1$=7 Hz, J$_2$=10 Hz, J$_3$=13 Hz, 1H), 2.24–2.14 (m, 1H), 1.88–1.58 (m's, 3H), 0.90 (d, J=7 Hz, 3H), 0.89 (d, J=7 Hz, 3H) and 0.84 (t, J=7 Hz, 3H) ppm.

b) N-[(3R,5R)-1-(Hydroxy)-5-isopropyl-2-oxopyrrolidinyl]-N-propyl-4'-(trifluoromethyl)[1,1'-biphenyl]-4-sulfonamide N-[(3R,5R)-1-(Benzyloxy)-5-isopropyl-2-oxopyrrolidinyl]-N-propyl-4'-(trifluoromethyl)[1,1'-biphenyl]-4-sulfonamide (0.015 g, 0.026 mmoles, Example 28b) in 5.0 mL methanol was hydrogenated on 5% Pd/BaSO$_4$ (0.005 g) at 1 atm H$_2$ and 22° C. After 6 hours the solution was filtered through Celite and concentrated by rotary evaporation to afford 0.012 g (95% yield) of the title compound as a white solid. LC-MS (APCI) m/z 485 (M+1). $^1$H NMR (CD$_3$OD) δ 8.07 (d, J=8 Hz, 2H), 7.89 (d, J=6 Hz, 2H), 7.87 (d, J=6 Hz, 2H), 7.79 (d, J=8 Hz, 2H), 4.69 (t, J=10 Hz, 1H), 3.57 (ddd, J$_1$=4 Hz, J$_2$=7 Hz, J$_3$=10 Hz, 1H), 3.10 (t, J=8 Hz, 2H), 2.30–2.18 (m, 2H), 1.81–1.57 (m's, 3H), 0.95 (d, J=7 Hz, 3H), 0.90 (d, J=7 Hz, 3H) and 0.85 (t, J=8 Hz, 3H) ppm.

EXAMPLE 29

N-[(3S)-1-hydroxy-2-oxopyrrolidinyl]-4'-(trifluoromethyl)[1,1'-biphenyl]-4-sulfonamide

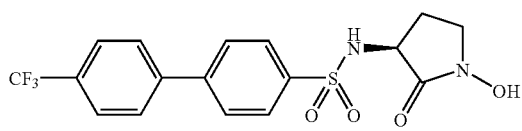

Prepared as described for the R-enantiomer in Example 15.

$^1$H NMR DMSOD$_6$: δ 1.60 (1H, sext); 2.03–2.10 (1H, m); 3.27–3.32 (2H, m); 4.00 (1H, t); 7.85 (2H, d); 7.93–7.98 (6H, m); 8.28 (1H, brs); 9.78 (1H, brs) APCI-MS m/z: 401 [MH+].

EXAMPLE 30

N-[(3S)-1-hydroxy-2-oxopyrrolidinyl]-N-methyl-4'-(trifluoromethyl)[1,1'-biphenyl]-4-sulfonamide

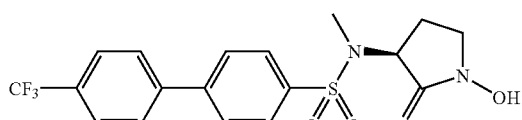

Prepared as described for the R-enantiomer in Example 20.

$^1$H NMR DMSOD$_6$: δ 1.76–1.85 (1H, m); 2.04–2.11 (1H, m); 2.65 (3H, s); 3.37 (2H, t); 4.76 (1H, t); 7.86 (2H, d); 7.97 (6H, d); 9.90 (1H, s) APCI-MS m/z: 415 [MH+].

EXAMPLE 31

N-[(3S)-1-hydroxy-2-oxopyrrolidinyl]-N-propyl-4'-(trifluoromethyl)[1,1'-biphenyl]-4-sulfonamide

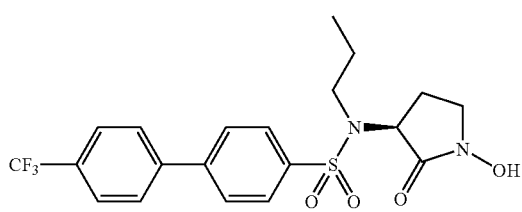

Prepared as described for the R-enantiomer in Example 23.

$^1$H NMR DMSOD$_6$: δ 0.79–0.85 (6H, m); 1.77–1.86 (1H, m); 1.86–1.96 (1H, m); 2.14–2.22 (1H, m); 2.86–2.97 (2H, m); 3.35–3.43 (2H, m); 4.59 (1H, t); 7.86 (2H, d); 7.93–8.01 (6H, m); 9.84 (1H, brs) APCI-MS m/z: 457 [MH+].

EXAMPLE 32

N-[(3S)-1-hydroxy-2-oxopyrrolidinyl][1,1'-biphenyl]-4-sulfonamide

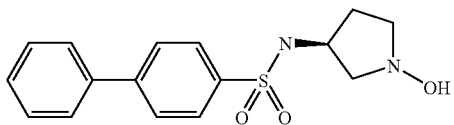

Prepared as described for the R-enantiomer in Example 12.

$^1$H NMR DMSOD$_6$: δ 1.54–1.63 (1H, m); 2.01–2.09 (1H, m); 3.26–3.33 (1H, m); 3.98 (1H, t); 7.43 (1H, t); 7.50 (2H, t); 7.73 (1H, d); 7.89 (4H, abq); 9.8 (1H, brs) APCI-MS m/z: 333 [MH+].

EXAMPLE 33

N-[(3S)-1-hydroxy-2-oxopyrrolidinyl]-N-methyl[1,1'-biphenyl]-4-sulfonamide

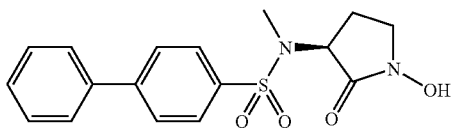

Prepared as described for the R-enantiomer in Example 19.

$^1$H NMR DMSOD$_6$: δ 1.73–1.83 (1H, m); 2.01–2.10 (1H, m); 2.64 (3H, s); 3.32–3.38 (2H, m, Partially obscured by HOD); 4.74 (1H, t); 7.44 (1H, t); 7.51 (2H, t); 7.74 (2H, d); 7.89 (4H, abq); 9.99 (1H, brs) APCI-MS m/z: 347 [MH+].

EXAMPLE 34

N-[(3S)-1-hydroxy-2-oxopyrrolidinyl]-N-propyl[1,1'-biphenyl]-4-sulfonamide

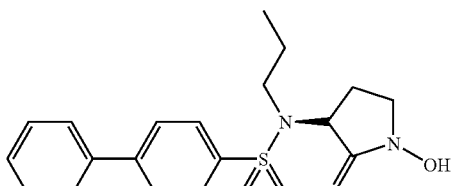

Prepared as described for the R-enantiomer in Example 22.

$^1$H NMR DMSOD$_6$: δ 0.78 (3H, t); 1.50–1.62 (2H, m); 1.82–1.91 (1H, m); 2.15–2.32 (1H, m); 2.90–3.06 (2H, m); 3.32–3.40 (2H, m, Partially obscured by HOD); 4.62 (1H, t); 7.44 (1H, t); 7.51 (2H, t); 7.86 (2H, d); 7.97 (2H, d); 9.86 (1H, brs) APCI-MS m/z: 375 [MH+].

What we claim is:

1. A compound of the formula I or a pharmaceutically acceptable salt or an in vivo hydrolysable ester thereof

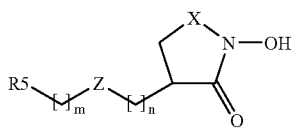

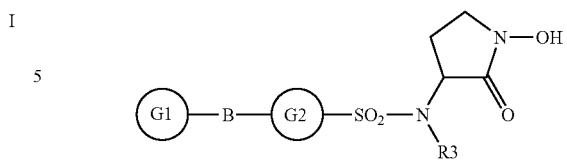

wherein
  X is selected from CO, CS or CR1R2;
  Z is selected from SO2N(R3) or N(R4)SO2
  n is 0;
  m is 0;
  R1 and R2 are each independently selected from H or C1–6 alkyl;
  R3 and R4 are each independently selected from H, C1–6 alkyl, phenyl-C1–6 alkyl, or heteroaryl-C1–6 alkyl;
  R5 is a dicyclic group of the following formula;

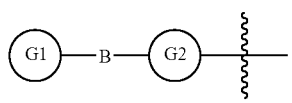

wherein G1 is phenyl or pyridyl; G2 is phenyl, piperidyl, piperazinyl, or pyrrolidinyl and B is a direct bond, wherein each of G1 and G2 is independently optionally substituted by one or more substituents independently selected from halogen, C1–6 alkyl, C2–6 alkenyl, C1–6 haloalkyl, C1–6 alkoxy, C1–6 haloalkoxy, thiolo, C1–6 thioloalkyl, C1–6 thiolo-haloalkyl, sulfono, C1–6 sulfonoalkyl, C1–6 sulfono-haloalkyl, aminosulfonyl, sulfoxy, C1–6 sulfoxyalkyl, amino, cyanoamino, hydrazine, C1–6 aminoalkyl, aminocarbonylamine, methylsulfonamine, acetamido, N-(C1–3 alkyl)acetamido, carboxamide, N(C1–3 alkyl)carboxamide, N,N -di-(C1–3 alkyl)carbamate, cyano, C1–6 cyanoalkyl, hydroxy, nitro, nitroso, formyl, N-methylformamide, methylformate, ethylformate, acetyl, acetoxy.

2. A compound as claimed in claim 1 or a pharmaceutically acceptable salt or an in vivo hydrolysable ester thereof wherein X is CO or CH2.

3. A compound as claimed in claim 1 or a pharmaceutically acceptable salt or an in vivo hydrolysable ester thereof wherein Z is SO2N(R3).

4. A compound as claimed in claim 1 or a pharmaceutically acceptable salt or an in vivo hydrolysable ester thereof wherein R3 is H, C1–6 alkyl, or phenyl-C1–6 alkyl.

5. A compound as claimed in claim 1 or a pharmaceutically acceptable salt or an in vivo hydrolysable ester thereof, wherein each of G1 and G2 is independently optionally substituted by one or more substituents independently selected from halogen, C1–6 alkyl, C1–6 haloalkyl, C1–6 alkoxy, C1–6 haloalkoxy, acetamido, N-C1–3 alkyl)acetamido, carboxamide, N(C1–3 alkyl)carboxamide, N,N -di-(C1–3 alkyl)carbamate or cyano.

6. A compound as claimed in claim 1 or a pharmaceutically acceptable salt or an in vivo hydrolysable ester thereof, wherein each of G1 and G2 is independently optionally substituted by one or two substituents independently selected from halogen, C1–6 alkyl, C1–6 haloalkyl, C1–6 alkoxy, C1–6 haloalkoxy.

7. A compound of claim 1 or a pharmaceutically acceptable salt or an in vivo hydrolysable ester thereof having the formula:

wherein
  R3 is selected from H, C1–6 alkyl or phenyl-C1–6 alkyl; and
  each of G1 and G2 is independently optionally substituted by one or two substituents independently selected from halogen, C1–6 alkyl, C1–6 haloalkyl, C1–6 alkoxy, or C1–6 haloalkoxy.

8. A compound as claimed in claim 7 or a pharmaceutically acceptable salt or an in vivo hydrolysable ester thereof wherein G1 is optionally substituted by halogen or C1–3 haloalkyl.

9. A compound as claimed in claim 7 or a pharmaceutically acceptable salt or an in vivo hydrolysable ester thereof wherein G2 is

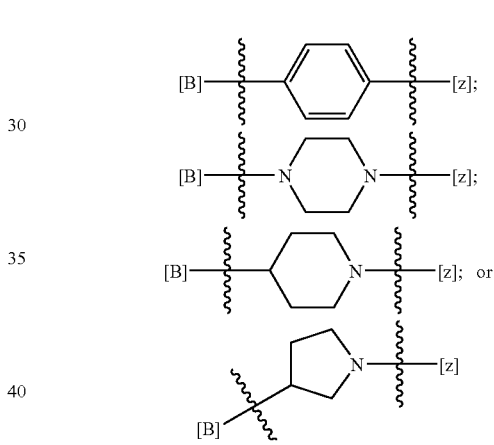

10. A pharmaceutical composition which comprises a compound of the formula I as claimed in claim 1 or a pharmaceutically acceptable salt or an in vivo hydrolysable ester thereof and a pharmaceutically acceptable carrier.

11. A pharmaceutical composition which comprises a compound of the formula II as claimed in claim 7 or a pharmaceutically acceptable salt or an in vivo hydrolysable ester thereof and a pharmaceutically acceptable carrier.

12. A method for the treatment of chronic obstructive pulmonary disease, COPD, which comprises administering to a human or animal in need thereof a therapeutically effective amount of a compound of the formula I as claimed in claim 1 or a pharmaceutically acceptable salt or an in vivo hydrolysable ester thereof.

13. A method for the treatment of chronic obstructive pulmonary disease, COPD, which comprises administering to a human or animal in need thereof a therapeutically effective amount of a compound of the formula II as claimed in claim 7 or a pharmaceutically acceptable salt or an in vivo hydrolysable ester thereof.

14. A method for the treatment of bronchitis, which comprises administering to a human or animal in need thereof a therapeutically effective amount of a compound of the formula I as claimed in claim 1 or a pharmaceutically acceptable salt or an in vivo hydrolysable ester thereof.

15. A method for the treatment of bronchitis, which comprises administering to a human or animal in need thereof a therapeutically effective amount of a compound of the formula II as claimed in claim 7 or a pharmaceutically acceptable salt or an in vivo hydrolysable ester thereof.

16. A method for the treatment of asthma, which comprises administering to a human or animal in need thereof a therapeutically effective amount of a compound of the formula I as claimed in claim 1 or a pharmaceutically acceptable salt or an in vivo hydrolysable ester thereof.

17. A method for the treatment of asthma, which comprises administering to a human or animal in need thereof a therapeutically effective amount of a compound of the formula II as claimed in claim 7 or a pharmaceutically acceptable salt or an in vivo hydrolysable ester thereof.

18. A method for the treatment of arthritis, which comprises administering to a human or animal in need thereof a therapeutically effective amount of a compound of the formula I as claimed in claim 1 or a pharmaceutically acceptable salt or an in vivo hydrolysable ester thereof.

19. The method of claim 18, wherein the arthritis is rheumatoid arthritis or osteoarthritis.

20. A method for the treatment of arthritis, which comprises administering to a human or animal in need thereof a therapeutically effective amount of a compound of the formula II as claimed in claim 7 or a pharmaceutically acceptable salt or an in vivo hydrolysable ester thereof.

21. The method of claim 20, wherein the arthritis is rheumatoid arthritis or osteoarthritis.

* * * * *